United States Patent
Suzuki

(10) Patent No.: US 9,779,520 B2
(45) Date of Patent: Oct. 3, 2017

(54) X-RAY COMPUTED TOMOGRAPHY SCANNER, DATA PROCESSING DEVICE, AND DATA PROCESSING METHOD

(75) Inventor: Tatsuro Suzuki, Utsunomiya (JP)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 591 days.

(21) Appl. No.: 12/724,609

(22) Filed: Mar. 16, 2010

(65) Prior Publication Data

US 2010/0239146 A1 Sep. 23, 2010

(30) Foreign Application Priority Data

Mar. 18, 2009 (JP) ................................. 2009-066737
Mar. 1, 2010 (JP) ................................. 2010-044414

(51) Int. Cl.
G06T 1/00 (2006.01)
A61B 6/03 (2006.01)
G06T 11/00 (2006.01)

(52) U.S. Cl.
CPC ............. *G06T 11/005* (2013.01); *A61B 6/032* (2013.01)

(58) Field of Classification Search
CPC ................. G06T 11/008; G06T 11/005; G06T 1/003–1/008
USPC ........................................................ 378/19
See application file for complete search history.

(56) References Cited

U.S. PATENT DOCUMENTS

| | | | | |
|---|---|---|---|---|
| 5,463,666 A * | 10/1995 | Eberhard et al. | ................. | 378/4 |
| RE36,162 E * | 3/1999 | Bisek et al. | ................. | 378/146 |
| 6,078,638 A * | 6/2000 | Sauer et al. | ...................... | 378/4 |
| 6,184,889 B1 * | 2/2001 | D'Amora | ...................... | 345/419 |
| 7,154,988 B2 * | 12/2006 | Sugihara et al. | ............... | 378/15 |
| 7,453,974 B2 * | 11/2008 | Van Steven-Daal et al. | .... | 378/6 |
| 7,747,057 B2 * | 6/2010 | Wu et al. | ...................... | 382/131 |
| 2004/0114717 A1 * | 6/2004 | Kato | ............................... | 378/62 |
| 2004/0208277 A1 | 10/2004 | Morikawa | | |

(Continued)

FOREIGN PATENT DOCUMENTS

| | | |
|---|---|---|
| JP | 2000-152926 A | 6/2000 |
| JP | 2004-57506 A | 2/2004 |
| JP | 2004-313655 A | 11/2004 |

(Continued)

OTHER PUBLICATIONS

Japanese Office Action with its English Translation for Japanese Patent Application No. 2010-044414 mailed on Oct. 15, 2013.

(Continued)

*Primary Examiner* — Dani Fox
(74) *Attorney, Agent, or Firm* — Kenichiro Yoshida

(57) ABSTRACT

A rotation frame supports an X-ray tube and an X-ray detector to be rotatable about a rotation axis. A top plate support mechanism supports the top plate on which a sample is placed to be movable along the rotation axis. A scan controller drives the top plate support mechanism and the rotation frame so as to scan a plurality of scan areas either partially overlapping or being adjacent along the rotation axis with the X-rays. A reconstruction processor generates a plurality of volume data sets corresponding to the plurality of scan areas on the basis of the output from the X-ray detector. A boundary corrector corrects CT values of the plurality of volume data sets on the basis of CT value differences between the overlapping or adjacent portions of the plurality of volume data sets.

28 Claims, 35 Drawing Sheets

(56) References Cited

U.S. PATENT DOCUMENTS

2007/0140416 A1* 6/2007 Nukui .............................. 378/19
2011/0228900 A1* 9/2011 Sakai .............................. 378/10

FOREIGN PATENT DOCUMENTS

| JP | 2006-239303 A | 9/2006 | | |
| JP | 2007-151849 A | 6/2007 | | |
| JP | 2007-190358 A | 8/2007 | | |
| WO | WO2008064367 | * | 5/2008 | ............... G06T 7/40 |

OTHER PUBLICATIONS

Japanese Office Action with its English translation for Japanese Patent Application No. 2010-044414 mailed on Feb. 4, 2014.
Japanese Office Action with its English summary for corresponding JP Patent Application No. 2014-173264 mailed on May 19, 2015.

* cited by examiner

FIG. 13
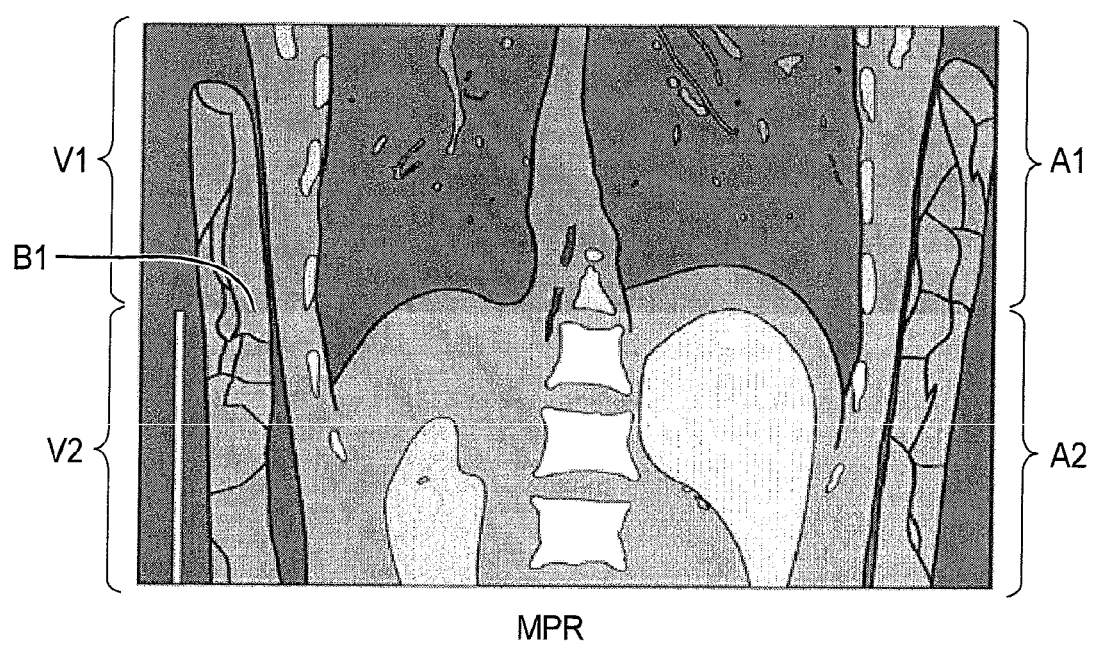
MPR
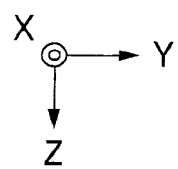

FIG. 14
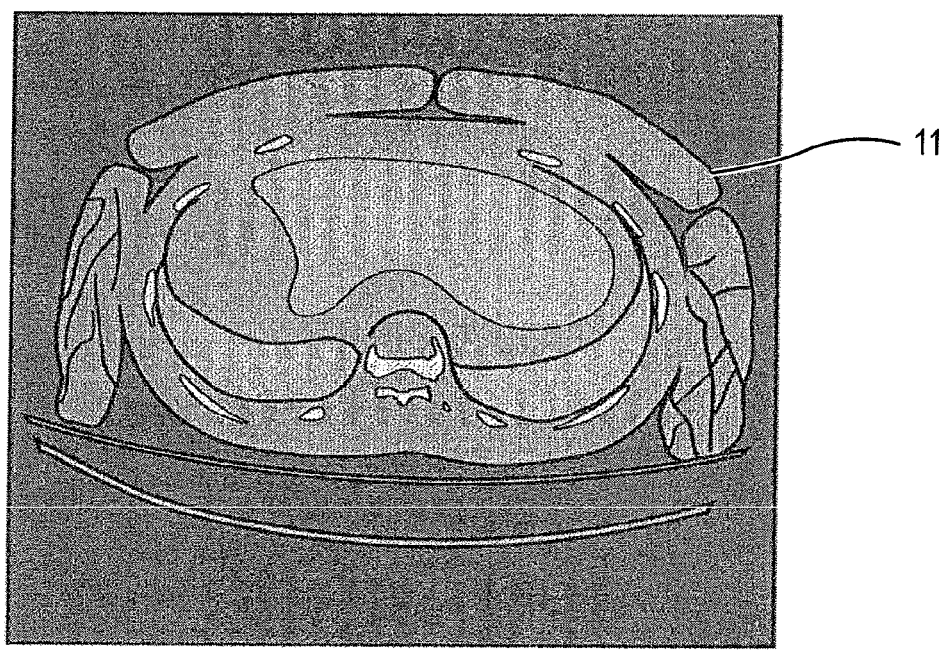
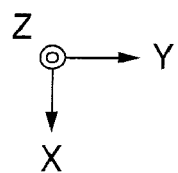

FIG. 15
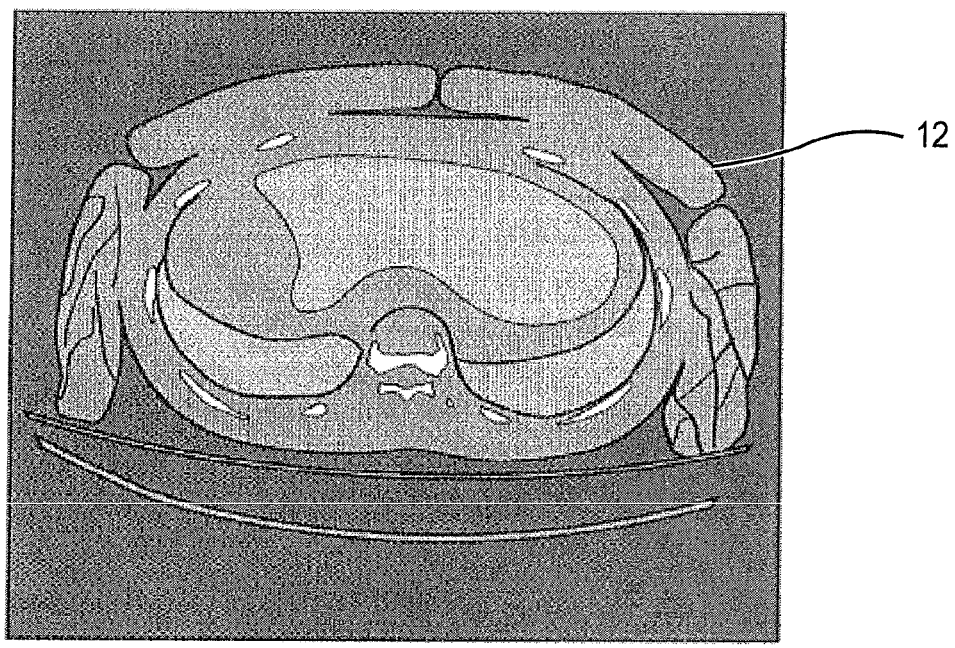
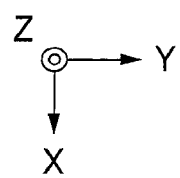

X-RAY COMPUTED TOMOGRAPHY SCANNER, DATA PROCESSING DEVICE, AND DATA PROCESSING METHOD

CROSS-REFERENCE TO RELATED APPLICATIONS

This application is based upon and claims the benefit of priority from prior Japanese Patent Applications No. 2009-066737, filed Mar. 18, 2009; and No. 2010-044414, filed Mar. 1, 2010, the entire contents of both of which are incorporated herein by reference.

BACKGROUND OF THE INVENTION

1. Field of the Invention

The present invention relates to an X-ray computed tomography scanner, a data processing device, and a data processing method.

2. Description of the Related Art

As a scan method using an X-ray computed tomography scanner (hereinafter, referred to as "X-ray CT scanner"), a scan method of alternately repeating a circular orbital scan (conventional scan) and a movement of a top plate on which a sample is placed is known, for example, as disclosed in JP-A-2006-239303. By using this scan method, a very broad area can be scanned by a cone-beam (also referred to as "multi-slice") CT. A circular orbital scan is a scan method of causing an X-ray tube to move in a circular orbit around a stationary sample.

The scanning process will be explained using the example of a triple pass circular orbital scan. First, the X-ray CT scanner performs a circular orbital scan on a first scan area of the sample, collects a projection data set from the first scan area, and reconstructs a volume data set from the first scan area on the basis of the collected projection data set. For example, the Feldkamp (FDK) reconstruction method is used as the reconstruction method. Then, the X-ray CT scanner moves the top plate relative to the X-ray tube and the X-ray detector to dispose the top plate at a second scan position. The X-ray CT scanner performs the circular orbital scan on a second scan area, collects a projection data set from the second scan area, and generates a volume data set from the second scan area. Then, the X-ray CT scanner moves the top plate relative to the X-ray tube and the X-ray detector to dispose the top plate at a third scan position. The X-ray CT scanner performs the circular orbital scan on a third scan area, collects a projection data set from the third scan area, and generates a volume data set from the third scan area.

However, the above-mentioned technique has the following problem. That is, even when the scan is performed under the same X-ray conditions, the CT value of the same anatomic site may be different during every scan for various reasons such as a scattered radiation distribution differences, radiation curing inside the sample caused by the X-rays, and an energy differences in the X-rays between cone-angle directions. As a result, the CT values in the boundary surface between the adjacent volume data sets may be discontinuous. Accordingly, differences in the CT values of the boundary surface between the adjacent volume data sets may result.

BRIEF SUMMARY OF THE INVENTION

An object of the invention is that it provides an X-ray CT scanner, a data processing device, and a data processing method which can reduce the discontinuities in CT values between volume data sets.

According to a first aspect of the invention, there is provided an X-ray computed tomography scanner including: an X-ray tube generating X-rays; an X-ray detector detecting the X-rays generated from the X-ray tube and transmitted by a sample; a first support mechanism supporting the X-ray tube and the X-ray detector to be rotatable about a rotation axis; a second support mechanism supporting the sample to be movable along the rotation axis; a controller controlling the first support mechanism and the second support mechanism so as to scan a plurality of scan areas partially overlapping or being adjacent along the rotation axis by a plurality of times; a generator generating a plurality of volume data sets corresponding to the plurality of scan areas on the basis of the output from the X-ray detector; and a boundary corrector correcting CT values of the plurality of volume data sets on the basis of the CT values in the boundaries between the plurality of volume data sets.

According to a second aspect of the invention, there is provided an X-ray computed tomography scanner including: an X-ray tube generating X-rays; an X-ray detector detecting the X-rays generated from the X-ray tube and transmitted by a sample; a first support mechanism supporting the X-ray tube and the X-ray detector to be rotatable about a rotation axis; a second support mechanism supporting the sample to be movable along the rotation axis; a controller controlling the first support mechanism and the second support mechanism so as to scan a plurality of scan areas overlapping or being adjacent along the rotation axis with the X-rays; a collector collecting projection data on the plurality of scan areas from the X-ray detector; and a boundary corrector correcting the projection data on overlapping or adjacent portions of the plurality of scan areas among the projection data on the basis of positions of the overlapping or adjacent portions along the rotation axis.

According to a third aspect of the invention, there is provided a data processing device including: a storage unit storing a plurality of volume data sets from a plurality of scan areas; and a boundary corrector correcting CT values of the plurality of volume data sets on the basis of the CT values of boundaries among the plurality of volume data sets.

According to a fourth aspect of the invention, there is provided a data processing method in an X-ray computed tomography scanner including: an X-ray tube generating X-rays; an X-ray detector detecting the X-rays generated from the X-ray tube and transmitted by a sample; a first support mechanism supporting the X-ray tube and the X-ray detector to be rotatable about a rotation axis; a second support mechanism supporting the sample to be movable along the rotation axis; and a controller controlling the first support mechanism and the second support mechanism so as to scan a plurality of scan areas located at different positions along the rotation axis with the X-rays. Here, the data processing method includes: generating a plurality of volume data sets from the plurality of scan areas on the basis of the output from the X-ray detector; and correcting CT values of the plurality of volume data sets on the basis of CT value differences between two overlapping or adjacent boundary surfaces among the plurality of volume data sets.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 13 is a diagram illustrating an MPR image (coronal section image) based on a first volume data set and a second volume data set before being subjected to the boundary correcting process in step ST7 of FIG. 2.

FIG. 14 is a diagram illustrating an axial section image based on the first volume data set before being subjected to the boundary correcting process in step ST7 of FIG. 2.

FIG. 15 is a diagram illustrating an axial section image based on the second volume data set before being subjected to the boundary correcting process in step ST7 of FIG. 2.

DETAILED DESCRIPTION OF THE INVENTION

Hereinafter, an X-ray CT scanner, a data processing device, and a data processing method according to exemplary embodiments of the invention will be described with reference to the accompanying drawings.

First Embodiment

Figure 1:
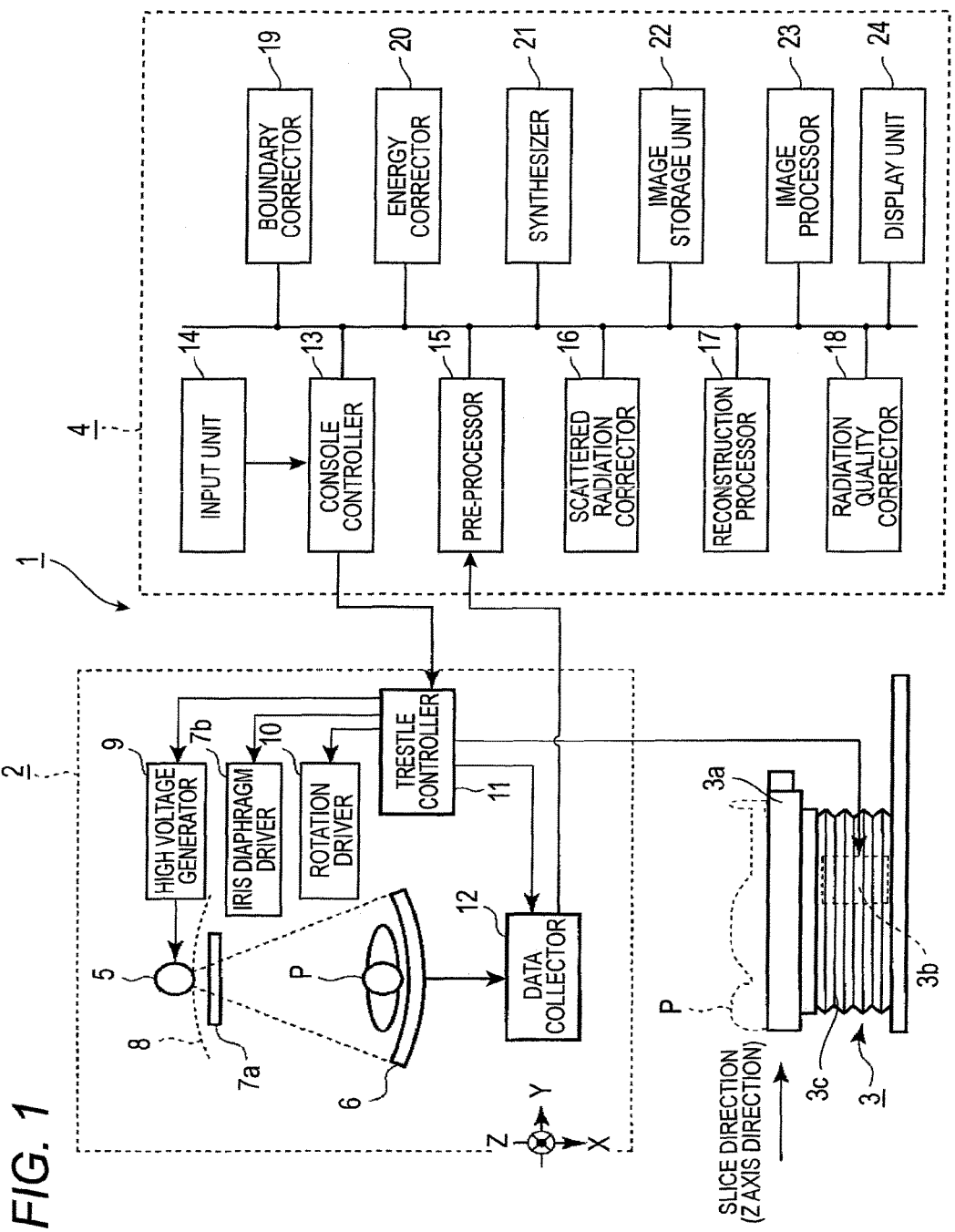
FIG. 1 is a diagram illustrating a configuration of an X-ray CT scanner according to a first embodiment of the invention.

FIG. 1 is a diagram illustrating a configuration of an X-ray CT scanner 1 according to a first embodiment of the invention. As shown in FIG. 1, the X-ray CT scanner 1 includes a trestle 2, a bed 3, and an operation console (data processing device) 4.

The trestle 2 includes an X-ray tube 5, an X-ray detector 6, an X-ray blocking plate 7a, an iris diaphragm driver 7b, a rotating frame 8, a high-voltage generator 9, a rotation driver 10, a trestle controller 11, and a data collector 12.

The X-ray tube 5 and the X-ray detector 6 are mounted on the rotating frame 8. By rotationally driving the rotating frame 8 by the use of the rotation driver 10, the X-ray tube 5 and the X-ray detector 6 go around a sample P in the state where they are opposed to each other.

The Z axis is defined by the rotation axis of the rotating frame 8. The X axis is defined by an axis which connects the focus of the X-ray tube 5 to the center of X-ray detector 6 and which is perpendicular to the Z axis. The Y axis is defined as an axis perpendicular to the X axis and the Z axis. In this way, the XYZ coordinate system constitutes a rotational coordinate system rotating with the rotation of the X-ray tube 5. The +Z direction and the −Z direction are called slice directions.

A support mechanism having the rotating frame 8 supports the X-ray tube 5 and the X-ray detector 6 to be rotatable about the sample. The support mechanism includes an electromotor rotating the rotating frame 8 with a supply of a driving signal from the rotation driver 10.

The X-ray tube 5 generates X-rays with an application of a tube voltage and a supply of a tube current from the high-voltage generator 9.

The X-ray detector 6 is a two-dimensional array detector (so-called multi-slice detector). The X-ray detector 6 includes plural X-ray detecting elements two-dimensionally arranged. The X-ray detecting element has a detection surface of, for example, 1 mm×1 mm square. For example, 1000 X-ray detecting elements are arranged along a circular arc about the Z axis. The arrangement direction of the X-ray detecting elements is called a channel direction. The X-ray detecting elements arranged in the channel direction are called an X-ray detecting element line. For example, 64 X-ray detecting element lines are arranged in the slice direction indicated by the Z axis.

An X-ray squeezing unit includes the X-ray blocking plate 7a and the iris diaphragm driver 7b. The X-ray squeezing unit has a function of adjusting a radiation range of the X-ray radiated to the sample P. For example, by moving the X-ray blocking plate 7a by the use of the iris diaphragm driver 7b, the X-ray radiation range in the slice direction can be adjusted.

The data collector (DAS) 12 reads an electric signal every channel from the X-ray detector 6, amplifies the read electric signal, and converts the amplified electric signal into a digital signal. The digital signal is called projection data. The projection data is supplied to the data processor 4. A projection data set means a set of projection data, which is necessary for reconstructing a volume, repeatedly collected while the X-ray tube 5 rotates by 360 degrees.

The bed 3 includes a top plate 3a, a top plate driver 3b, and a top plate support mechanism 3c. The sample P is placed on the top plate 3a. The top plate support mechanism 3c supports the top plate 3a to be movable along the Z axis.

Typically, the top plate support mechanism 3c supports the top plate 3a so that the major axis of the top plate 3a is parallel to the Z axis. The top plate driver 3b drives the top plate support mechanism 3c in accordance with a control signal from the trestle controller 11 and moves the top plate 3a in the slice direction. A bore is formed at the center of the rotating frame 8. The top plate 3a having the sample P placed thereon is inserted into the bore.

The operation console 4 includes a console controller 13, an input unit 14, a pre-processor 15, a scattered radiation corrector 16, a reconstruction processor 17, a radiation quality corrector 18, a boundary corrector 19, an energy corrector 20, a synthesizer 21, an image storage unit 22, an image processor 23, and a display unit 24.

The console controller 13 serves as a control core of the X-ray CT scanner 1. For example, the console controller 13 controls the trestle controller 11 to scan plural scan areas with the X-rays. Under the control of the console controller 13, the trestle controller 11 controls the top plate driver 3b, the iris diaphragm driver 7b, the high-voltage generator 9, the rotation driver 10, and the data collector 12. The console controller 13 and the trestle controller 11 constitute a scan controller.

The input unit 14 receives various instructions or information input from an operator. The input unit 14 may include a keyboard, a mouse, or a switch.

The pre-processor 15 performs pre-processes such as algebraic transformation or sensitivity correction on the projection data set output from the data collector 12.

The scattered radiation corrector 16 removes a scattered radiation component included in the projection data set on the basis of the projection values of the projection data set in the X-ray radiation range. Specifically, the scattered radiation corrector 16 calculates the scattered radiation component on the basis of the projection values of the projection data set of which the scattered radiation should be corrected or the projection data set adjacent thereto, and subtracts the calculated scattered radiation component from the projection data set of which the scattered radiation should be corrected.

The reconstruction processor 17 generates an image data set (volume data set) of biological information inside the sample P from the projection data set by the use of an image reconstruction method such as a fan-beam reconstruction method or a cone-beam reconstruction method. The fan-beam reconstruction method is an image reconstructing method in which it is assumed that X-ray passes in the slice direction are parallel to each other. The cone-beam reconstruction method is an image reconstructing method in which an X-ray radiation angle (a wide angle of an X-ray in the slide direction: cone angle) in the slice direction is considered. For example, the Feldkamp (FDK) reconstruction method is used as the image reconstructing method.

The volume data set includes data of plural axial section images arranged along the Z axis. The axial section image corresponds to a sectional surface parallel to the XY plane. The axial section image has, for example, a pixel size of 512×512. The volume data set includes 128 axial section images.

As described above, in the first embodiment, the plural scan areas are scanned. Accordingly, the reconstruction processor 17 generates plural volume data sets on the plural scan areas on the basis of the plural projection data sets on the plural scan areas.

The radiation quality corrector 18 performs a radiation quality correcting process on the plural volume data sets. A beam curing correction process such as a $2^{nd}$_pass_BCC (2nd BCC) process is used as the radiation quality correcting process. The radiation quality corrector 18 calculates a correction amount for the radiation quality correcting process and corrects the CT values of the volume data sets on the basis of the calculated correction amount.

The boundary corrector 19 corrects the CT values of the plural volume data sets on the basis of the CT values of the boundaries between the plural volume data sets. The boundary means an overlapping portion of two volume data sets or an adjacent portion of two volume data sets. Specifically, the boundary corrector 19 corrects the CT values of the plural volume data sets on the basis of the CT value difference between the pixels at the same position in the boundaries of the plural volume data sets.

The energy corrector 20 performs an energy correcting process on a volume data set. Specifically, the energy corrector 20 calculates a correction amount for the energy correcting process and corrects the CT values of the volume data set on the basis of the calculated correction amount.

The synthesizer 21 synthesizes the plural volume data sets to generate a single volume data set on all the scan areas. Hereinafter, the volume data set generated by the synthesizer 21 is referred to as a synthesized volume data set.

The image storage unit 22 stores the projection data sets, the volume data sets, and the synthesized volume data set.

The image processor 23 performs various image processes on the volume data sets or the synthesized volume data set to generate data of a display image. Various setting conditions and areas of interest at the time of generating a display image are set on the basis of the operator's input to the input unit 14.

The display unit 24 displays the display image.

The operation console 4 may be embodied by exclusive hardware or the same function may be embodied by software installed in a computer.

Figure 2:
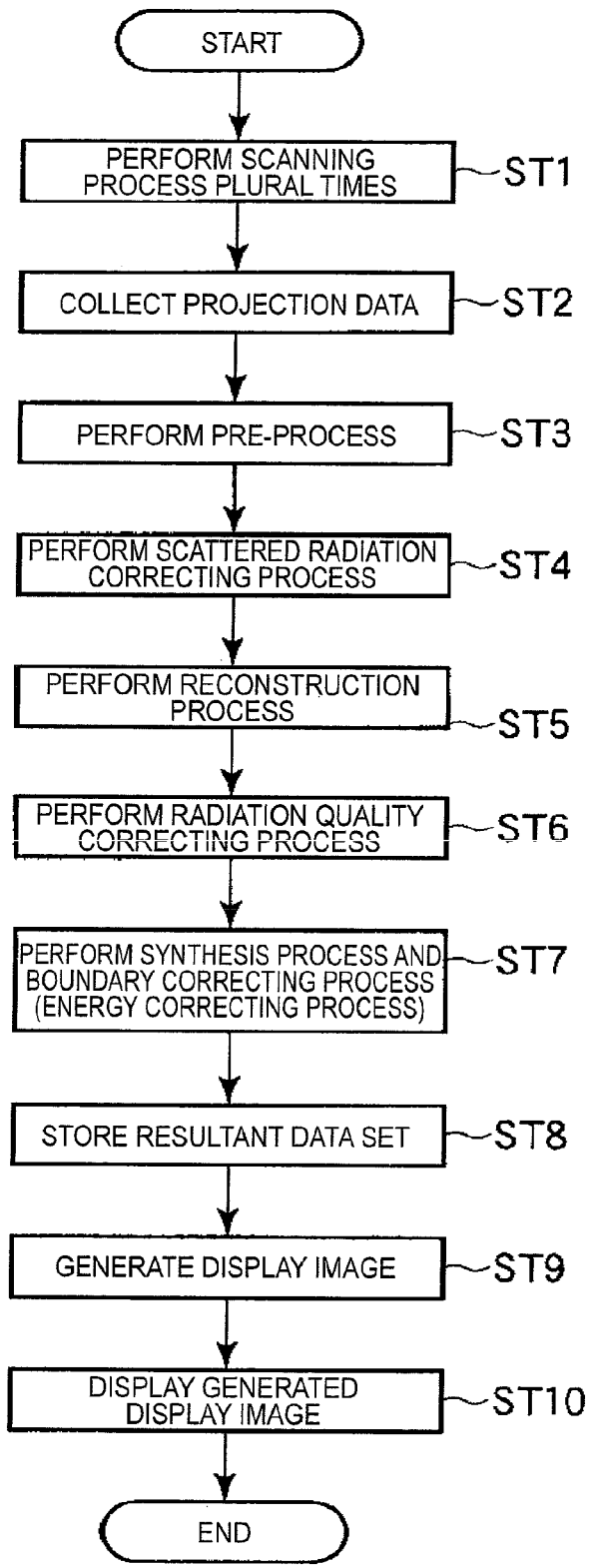
FIG. 2 is a diagram illustrating a typical flow of operations in the X-ray CT scanner according to the first embodiment.

Operations of the X-ray CT scanner 1 according to the first embodiment of the invention will be described. FIG. 2 is a diagram illustrating a typical flow of operations which are performed by the X-ray CT scanner 1 under the control of the console controller 13.

Figure 3:
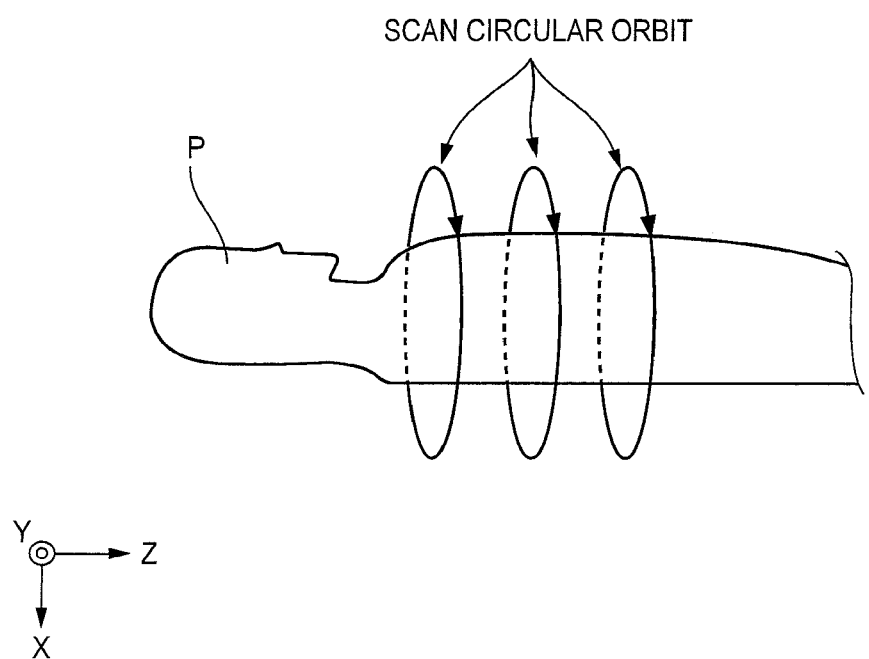
FIG. 3 is a diagram illustrating a positional relation of three circular orbital scans performed in step ST1 of FIG. 2.

As shown in FIG. 2, in step ST1, the console controller 13 indirectly controls the units of the trestle 2 via the trestle controller 11 to scan plural scan areas with X-rays. The trestle controller 11 controls the top plate driver 3b, the iris diaphragm driver 7b, the high-voltage generator 9, the rotation driver 10, and the data collector 12 under the control of the console controller 13. Under this control, the console controller 13 repeats the circular orbital scan and the movement of the sample P and scans the plural scan areas with the X-rays. In the following description, as shown in FIG. 3, it is assumed that three times of circular orbital scans are performed on the sample P.

Specifically, in step ST1, the rotation driver 10 drives the rotating frame 8 to rotate the X-ray tube 5 and the X-ray detector 6 about the Z axis. During the rotation, the X-ray tube 5 generates X-rays with the supply of a high voltage from the high-voltage generator 9. The X-ray blocking plate 7a restricts a steric angle of the X-rays to the radiation range corresponding to the scan condition.

In step ST2, the data collector 12 collects projection data via the X-ray detector 6. More specifically, the data collector 12 amplifies an electric signal output every channel from the X-ray detector 6 and converts the amplified electric signal into the projection data. The projection data is supplied to the operation console 4.

Figure 4:
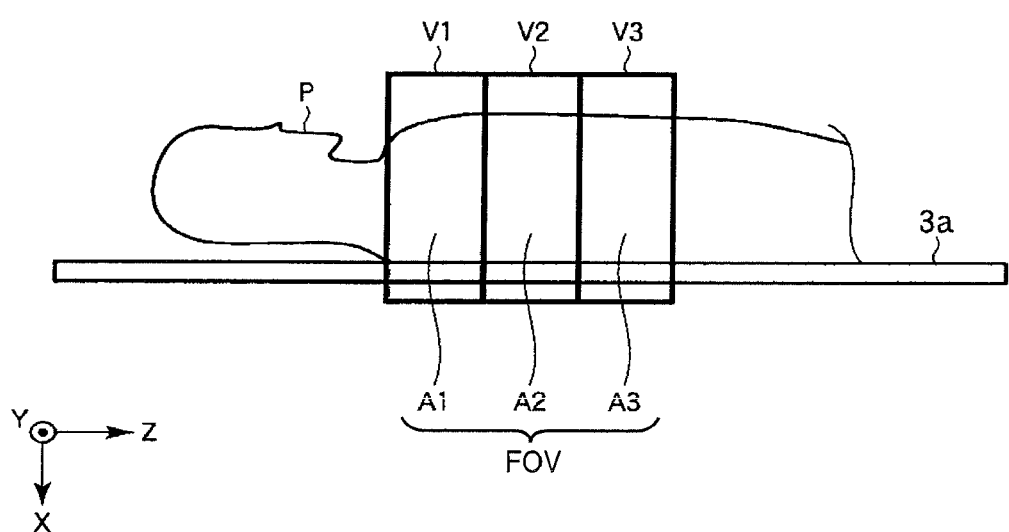
FIG. 4 is a diagram illustrating a positional relation of the scan area for a first circular orbital scan, the scan area for a second circular orbital scan, and the scan area for a third circular orbital scan in step ST1 of FIG. 2.

As shown in FIG. 4, an imaging area FOV on three times of circular orbital scans includes a first scan area A1, a second scan area A2, and a third scan area A3 which are arranged in the slice direction. Three scan areas A1, A2, and A3 are arranged to partially overlap with each other or to be adjacent to each other. Each of the scan areas A1, A2 and A3 is scanned by a one (one-rounding) circular orbital scan (a scan in a state where the top plate 3a is not moved in the slice direction, that is, a non-helical scan). Three times of circular orbital scans which are discontinuous provide three projection data sets corresponding to the scan areas A1, A2, and A3. Three volume data sets are reconstructed on the basis of the three projection data sets. Each volume data set includes plural axial section images.

Figure 5:
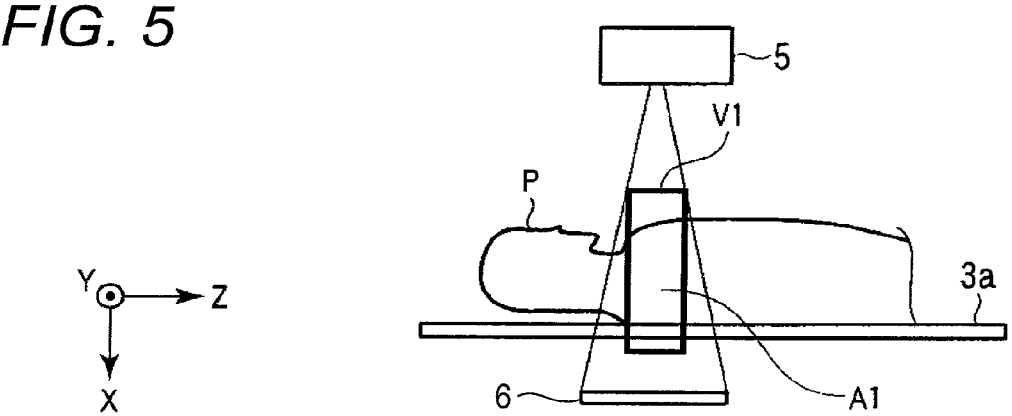
FIG. 5 is a diagram schematically illustrating the circular orbital scan on a first scan area in step ST1 of FIG. 2.
Figure 6:
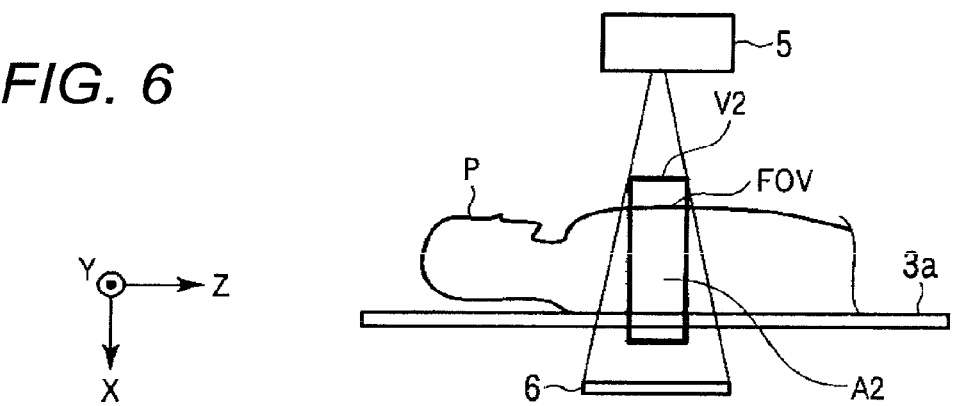
FIG. 6 is a diagram schematically illustrating the circular orbital scan on a second scan area in step ST1 of FIG. 2.
Figure 7:
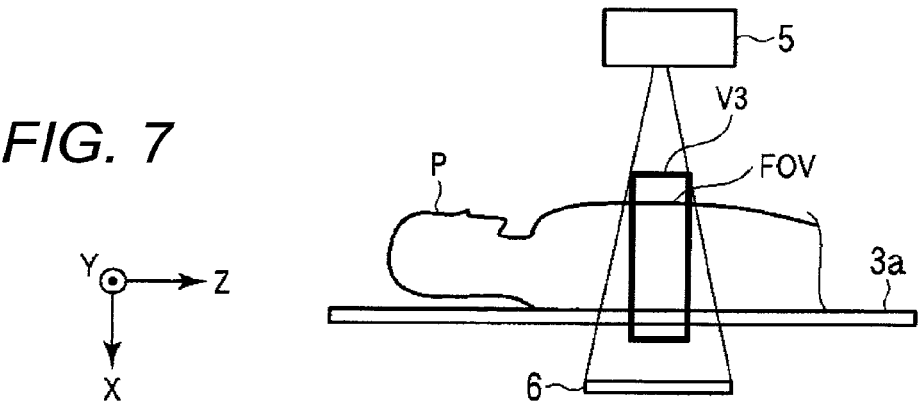
FIG. 7 is a diagram schematically illustrating the circular orbital scan on a third scan area in step ST1 of FIG. 2.

More specifically, in step ST1, the console controller 13 performs a first circular orbital scan on the first scan area A1 of the sample P, as shown in FIG. 5. When the first circular orbital scan is finished, the console controller 13 moves the top plate 3a having the sample (human body) P placed thereon in the slice direction and disposes the top plate 3a at the scan position of the second scan area A2. Then, the console controller 13 performs a second circular orbital scan on the second scan area A2, as shown in FIG. 6. When the second circular orbital scan is finished, the console controller 13 moves the top plate 3a in the slice direction and disposes the top plate 3a at the scan position of the third scan area A3. Then, the console controller 13 performs a third circular orbital scan on the third scan area A3, as shown in FIG. 7.

Figure 8:
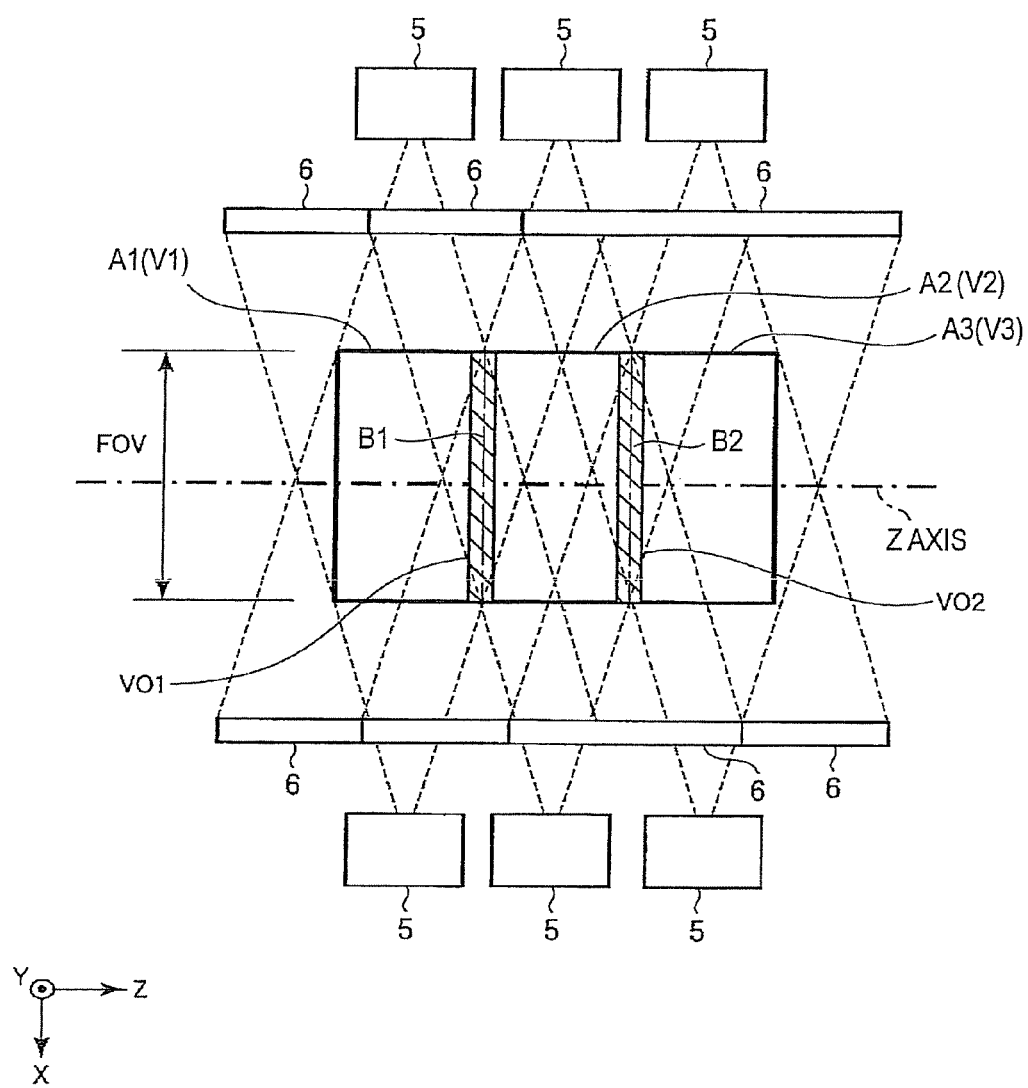
FIG. 8 is a diagram illustrating another positional relation of the first scan area, the second scan area, and the third scan area in step ST1 of FIG. 2.

As shown in FIG. 8, the imaging area FOV has a cylindrical shape centered on the Z axis. As described above, the imaging area FOV includes the first scan area A1, the second scan area A2, and the third scan area A3. Three scan areas A1, A2, and A3 partially overlap. Each of the overlapping portions VO1 and VO2 includes at least one axial section image.

That is, two axial section images of the same portion in the boundary surface B1 of the first scan area and the second scan area exist in the axial section images acquired by the first circular orbital scan and the axial section images acquired by the second circular orbital scan. Similarly, two axial section images of the same portion in the boundary surface B2 of the second scan area and the third scan area exist in the axial section images acquired by the second circular orbital scan and the axial section images acquired by the third circular orbital scan.

When the scan areas A1, A2, and A3 are arranged to be right adjacent to each other, the correction amount for the boundary correcting process is calculated using the axial section images of the adjacent portions of three volume data sets.

In step ST3, the pre-processor 15 performs pre-processes such as algebraic transformation or sensitivity correction on the projection data set output from the data collector 12. The projection data set having been subjected to the pre-processes is supplied to the scattered radiation corrector 16.

Figure 9:
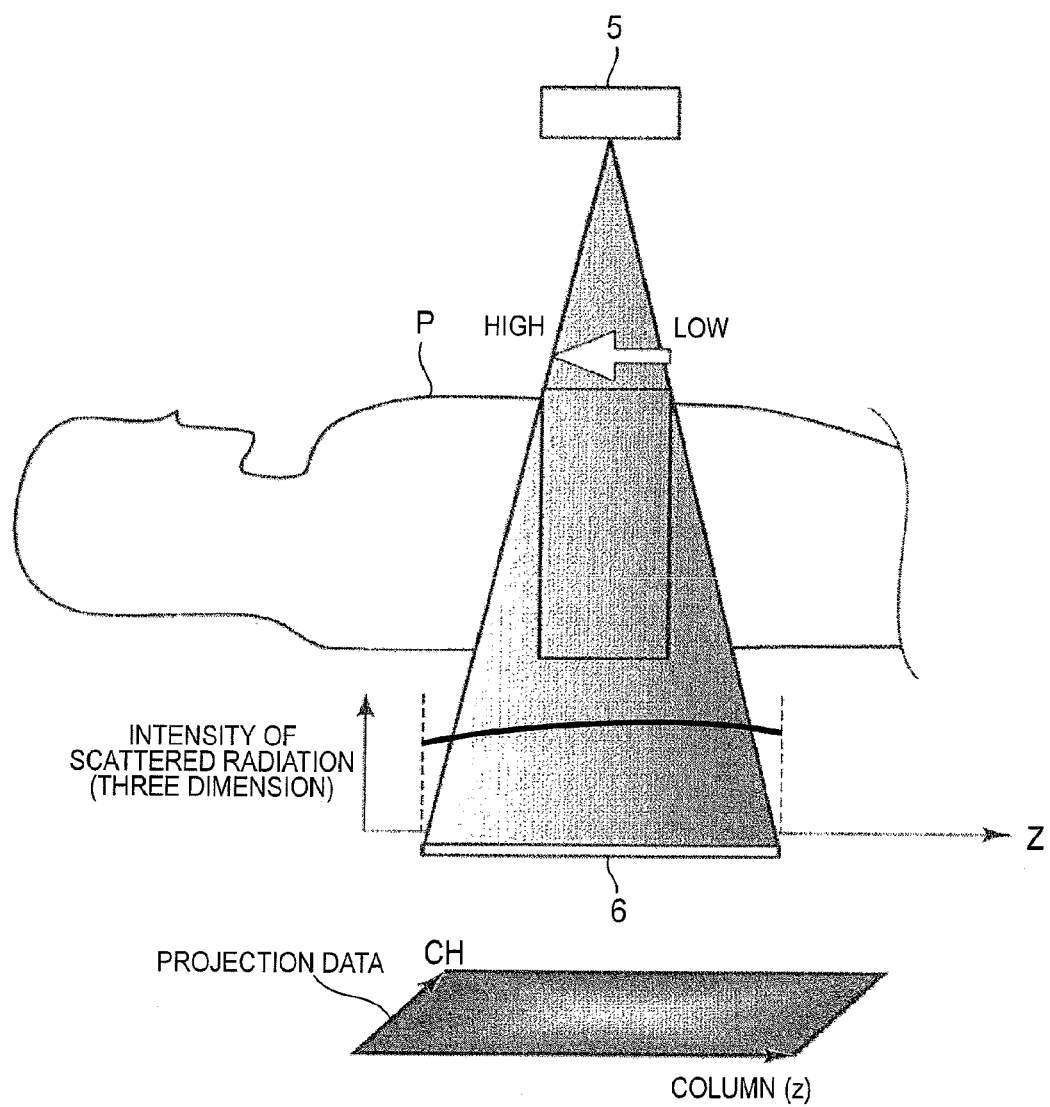
FIG. 9 is a diagram illustrating a scattered radiation correcting process performed by a scattered radiation corrector in step ST4 of FIG. 2.

In step ST4, the scattered radiation corrector 16 removes a scattered radiation component included in the projection data set. As shown in FIG. 9, the scattered radiation is generated, for example, by materials in the X-ray projection pass. Accordingly, a scattered radiation distribution difference is caused, for example, depending on the structure or site of the sample P. The scattered radiation is a reason of an artifact. Accordingly, to reduce the artifact resulting from the scattered radiation, the scattered radiation corrector 16 performs the scattered radiation correcting process on the projection data set. Specifically, the scattered radiation corrector 16 calculates an estimated scattered radiation component value on the basis of the projection values of the projection data to be corrected in scattered radiation or the adjacent projection data. The scattered radiation corrector 16 subtracts the calculated estimated scattered radiation component value from the projection value of the projection data to be corrected in scattered radiation, so as to perform the scattered radiation correcting process on the projection data to be corrected in scattered radiation. The projection data sets having been subjected to the scattered radiation correcting process are supplied to the reconstruction processor 17.

Figure 10:
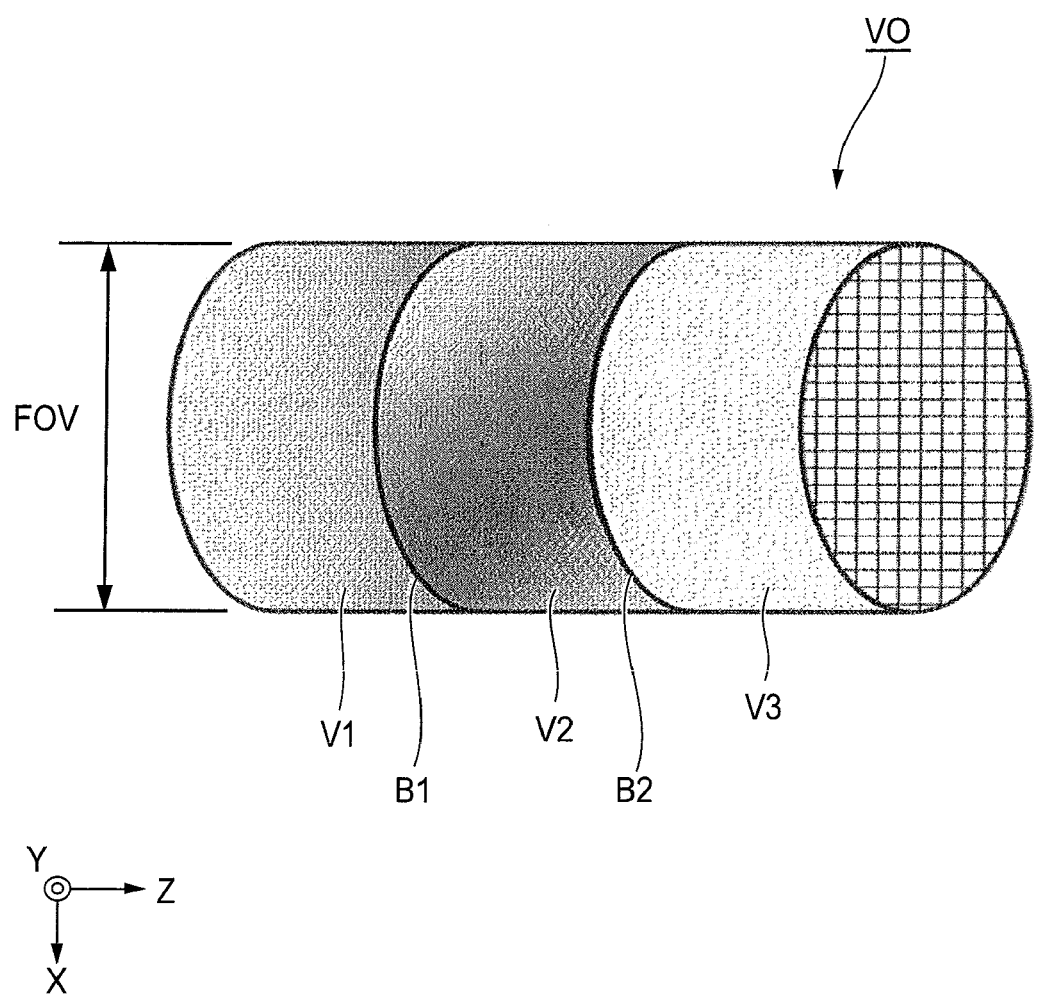
FIG. 10 is a diagram schematically illustrating a first volume data set, a second volume data set, and a third volume data set generated in step ST5 of FIG. 2.

In step ST5, the reconstruction processor 17 generates a first volume data set V1 from the projection data set on the first scan area A1 by the use of the reconstruction method such as the Feldkamp (FDK) reconstruction method, generates a second volume data set V2 from the projection data set on the second scan area A2, and generates a third volume data set V3 from the projection data set on the third scan area A3. As shown in FIG. 10, the volume data sets V1, V2, and V3 correspond to the cylindrical shapes, respectively. The reconstructed volume data sets V1, V2, and V3 are supplied to the radiation quality corrector 18.

In step ST6, the radiation quality corrector 18 performs the radiation quality correcting process such as the $2^{nd}$ BCC on the volume data sets so as to correct the X-ray radiation curing resulting from the structure of the sample P. An example of the radiation quality correcting process using the $2^{nd}$ BCC will be described below. First, the radiation quality corrector 18 reconstructs an original image on the basis of the projection data sets on the image display area (FOV) predetermined via the input unit 14. The radiation quality corrector 18 calculates the X-ray pass length of a bone and the X-ray pass length of an inorganic material such as water in the reconstructed original image. The radiation quality corrector 18 calculates an amount of beam curing in the bone and an amount of beam curing in the inorganic material such as water. The radiation quality corrector 18 calculates the projection data set of the correction component on the basis of the amount of beam curing in the bone and the amount of beam curing in the inorganic material. Then, the radiation quality corrector 18 reconstructs a corrected image on the basis of the projection data set of the correction component. The radiation quality corrector 18 generates an image corrected in BHC on the basis of the corrected image and the original image. Specifically, the radiation quality corrector 18 adds the corrected image and the original image to generate the image corrected in BHC. The data of the image corrected in BHC is supplied to the boundary corrector 19 and the energy corrector 20.

In step ST7, the synthesizer 21 synthesizes the volume data set V1, the volume data set V2, and the volume data set V3 to generate the single synthesized volume data set V0 of the imaging area FOV. The boundary correcting process in the boundary corrector 19 is included in the synthesis process. In step ST7, the boundary corrector 19 performs the boundary correcting process on the volume data set V1, the volume data set V2, and the volume data set V3 having been subjected to the radiation quality correcting process. The boundary correcting process in the boundary corrector 19 will be described later.

Figure 11:
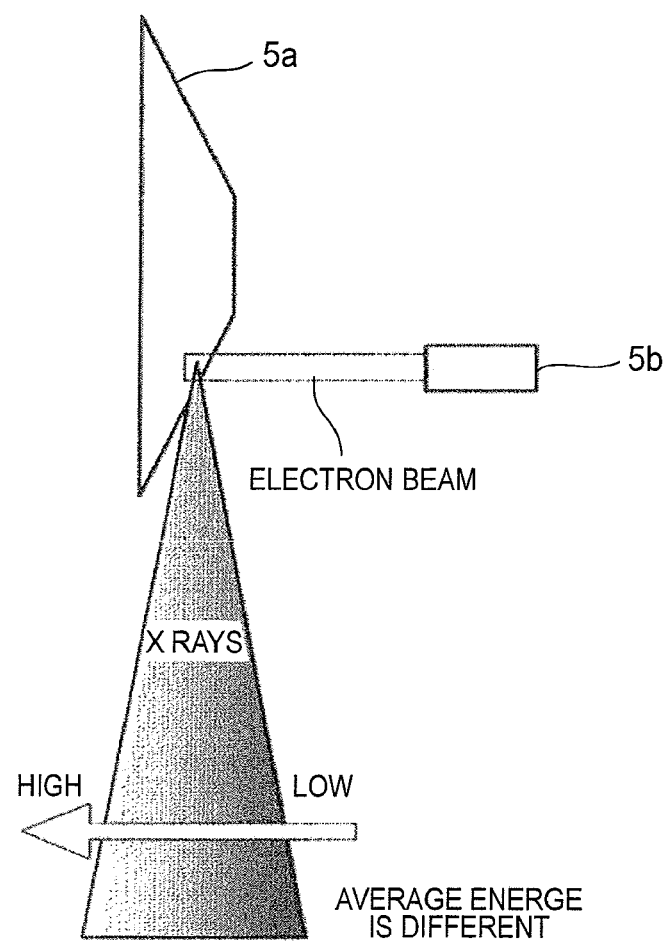
FIG. 11 is a diagram illustrating an energy correcting process performed by an energy corrector in step ST6 of FIG. 2.

An X-ray energy correcting process in the energy corrector 20 is included in the synthesis process in the synthesizer 21. The X-ray energy correcting process in the energy corrector 20 will be described. The X-rays can be more easily absorbed with the lower energy and can be more easily transmitted with the higher energy. As shown in FIG. 11, the electron beam from a cathode 5b of the X-ray tube 5 collides with an anode 5a. The dose of the low-energy X-ray absorbed by the anode 5a is different depending on the pass length of the electron beam in the anode 5a. Accordingly, the energy distribution of the X-rays generated from the X-ray tube 5 is non-uniform. By this influence, the CT values vary depending on the position of the X-ray detecting element line of the X-ray detector 6. In step ST7, the energy corrector 20 performs a correction process to remove the CT value differences between the images at both ends in the slice direction of the multi-slice X-ray detector 6.

Figure 12:
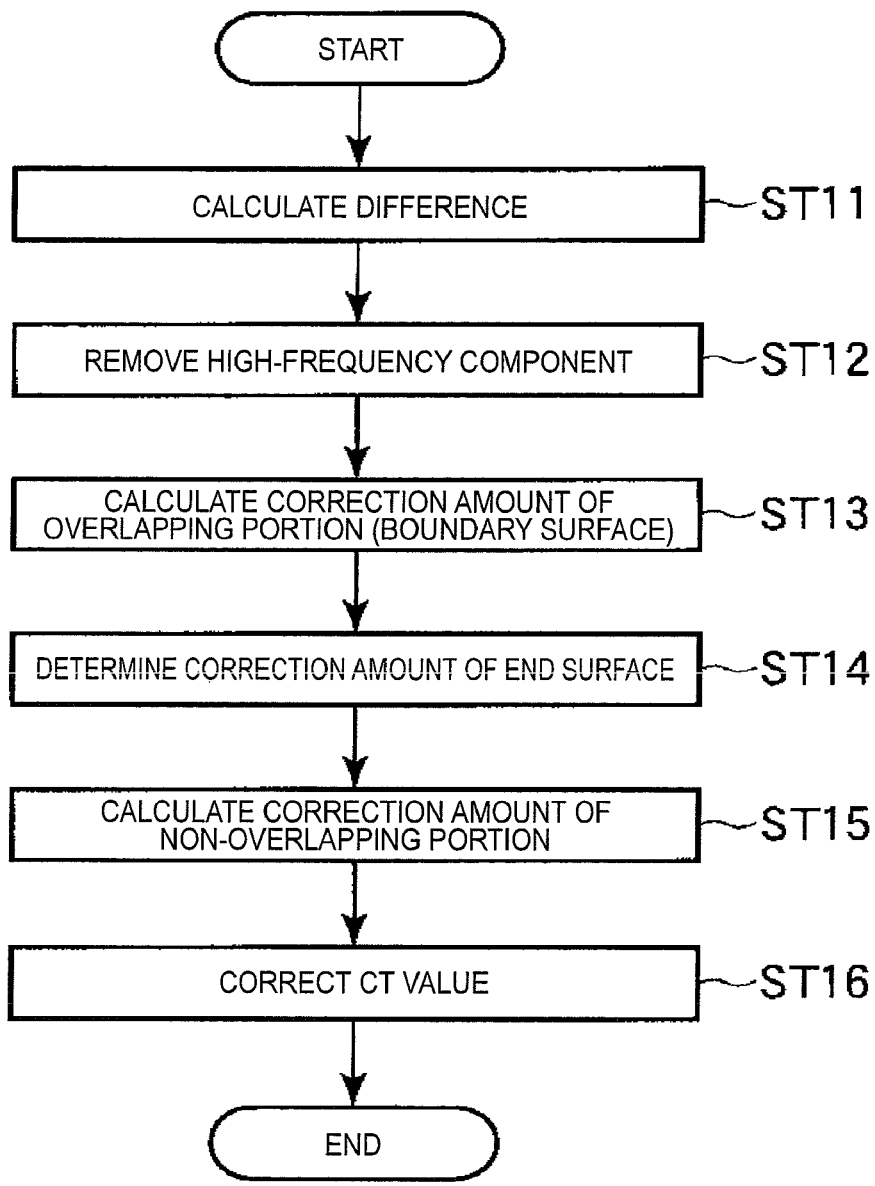
FIG. 12 is a diagram illustrating a typical flow of a boundary correcting process performed by a boundary corrector of FIG. 1 in step ST7 of FIG. 2.

The typical flow of the boundary correcting process performed by the boundary corrector 19 in step ST7 will be described. FIG. 12 is a diagram illustrating the typical flow of the boundary correcting process.

FIG. 13 is a diagram schematically illustrating an MPR image (coronal section image) based on the first volume data set V1 and the second volume data set V2 before being subjected to the boundary correcting process. The coronal section corresponds to the YZ plane. As shown in FIG. 13, a step difference in CT value is generated in the boundary surface B1 between the first volume data set V1 and the second volume data set V2. FIG. 14 shows an axial section image I1 of the boundary surface B1 included in the first volume data set V1. FIG. 15 shows an axial section image I2 of the boundary surface B1 included in the second volume data set V2.

Figure 16:
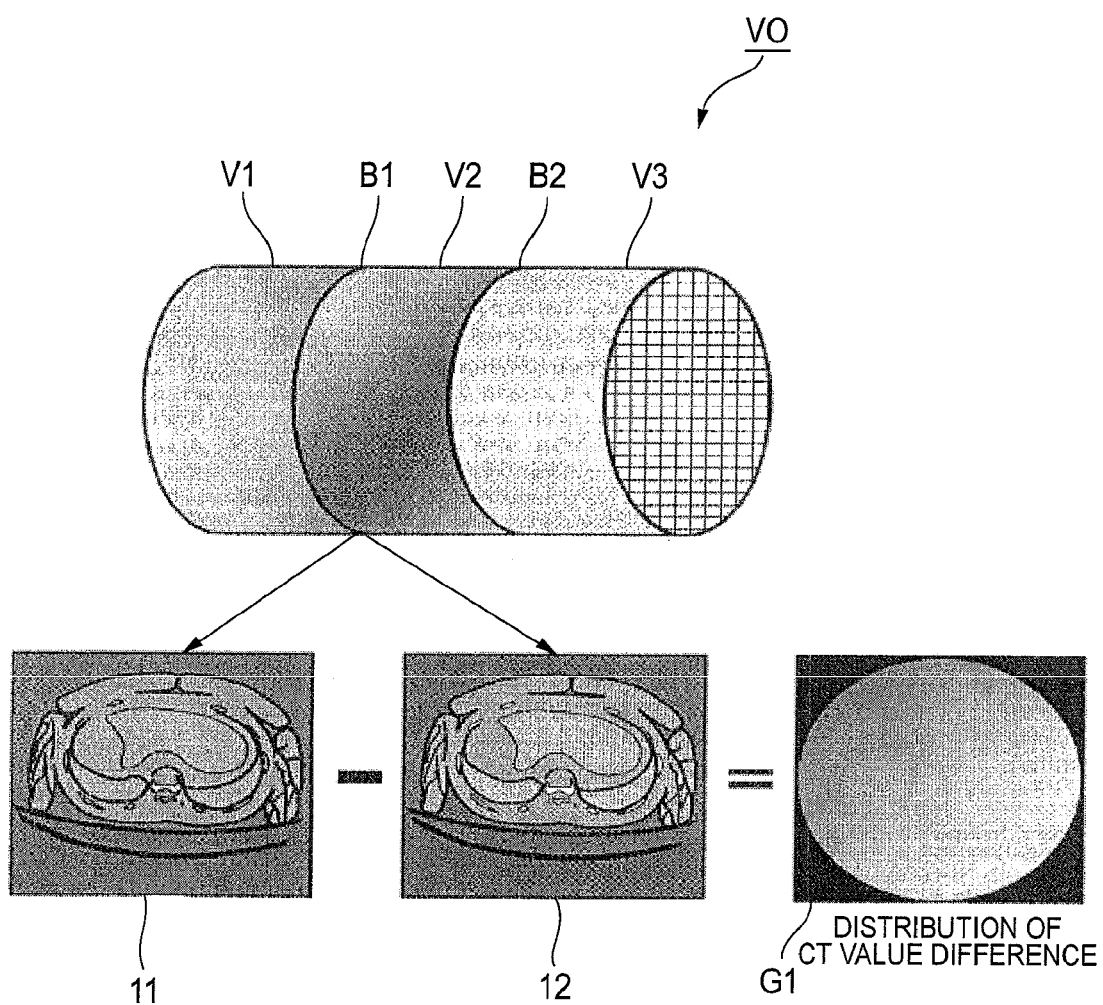
FIG. 16 is a diagram illustrating a process of calculating a CT value difference distribution, which is performed in step ST11 of FIG. 12.

First, in step ST11, the boundary corrector 19 generates a CT value differences distribution from two axial section images I (I1 and I2) on a single boundary surface between two volume data sets V (V1 and V2), as shown in FIG. 16. One of the two axial section images is included in the first volume data set V1. The other of the two axial section images is included in the second volume data set V2. That is, the axial section image I1 and the axial section image I2 overlap with each other. The boundary corrector 19 generates the CT value difference distribution G1 between the axial section image I1 and the axial section image I2 on the same anatomic section. Plural CT value differences are calculated by subtracting the plural CT values of the plural pixels constituting the axial section image I2 from the plural CT values of the plural pixels constituting the axial section image I1 by pixel positions. The CT value difference distribution G1 is defined as a spatial distribution of plural CT value differences.

Figure 17:
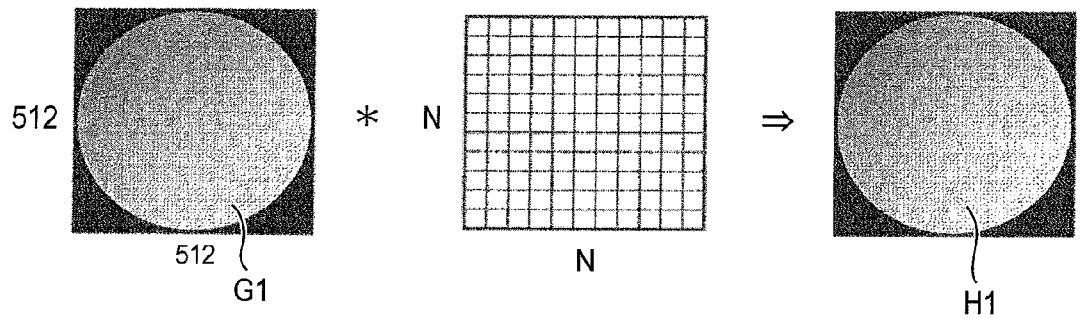
FIG. 17 is a diagram illustrating a high-frequency component removing or reducing process on a boundary surface between the first volume data set and the second volume data set, which is performed in step ST12 of FIG. 12.

In this way, the boundary corrector 19 can generate the CT value difference distribution G1 of the boundary surface B1, as shown in FIG. 17. The numerical expression of this process is G1=I1−I2.

Similarly, the boundary corrector 19 generates the CT value difference distributions of all the boundary surfaces. That is, the boundary corrector 19 generates the CT value difference distribution G2 of the boundary surface B2 between the volume data set V2 and the volume data set V3. The numerical expression of this process is G2=I2−I3.

Figure 18:
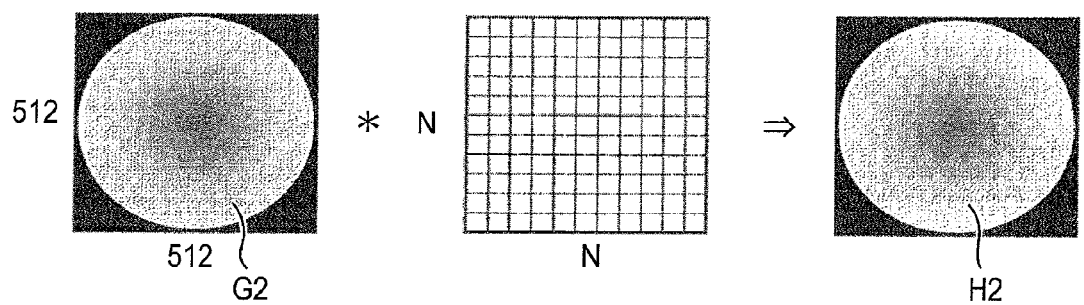
FIG. 18 is a diagram illustrating the high-frequency component removing or reducing process on a boundary surface between the second volume data set and the third volume data set, which is performed in step ST12 of FIG. 12.
Figure 19:
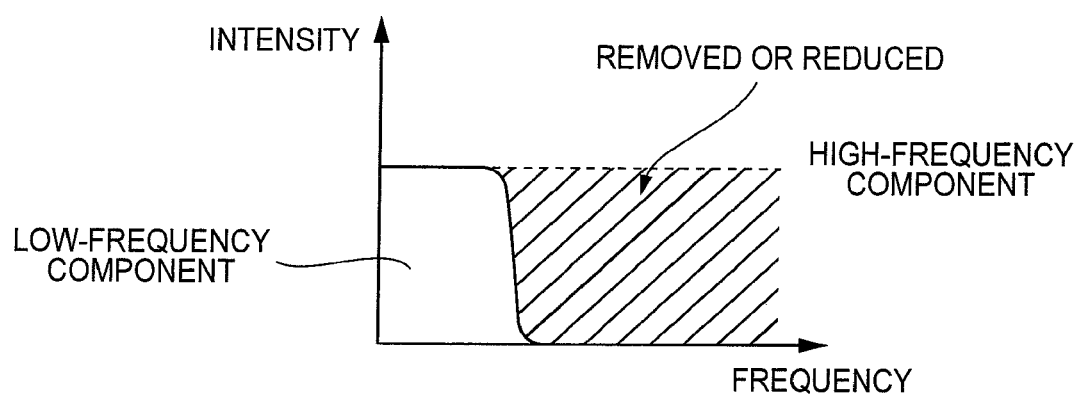
FIG. 19 is a diagram illustrating a low-pass filter in step ST12 of FIG. 12.

In step ST12, the boundary corrector 19 reduces or removes a high-frequency component from the CT value difference distributions. Basically, the CT value difference distributions do not have the high-frequency component. Accordingly, the boundary corrector 19 applies a low-pass filter having an N×N matrix to the entire surfaces of the CT value difference distributions G1 and G2, as shown in FIGS. 17 and 18. The boundary corrector 19 generates a CT value difference distribution H1 from which the high-frequency component is reduced or removed by applying the low-pass filter to the CT value difference distribution G1. Similarly, the boundary corrector 19 generates a CT value difference distribution H2 from which the high-frequency component is reduced or removed by applying the low-pass filter to the CT value difference distribution G2. The low-pass filter reduces or removes the high-frequency component included in the CT value difference distributions G1 and G2 without changing the intensity of low-frequency components included in the CT value difference distributions G1 and G2, as shown in FIG. 19.

Figure 20:
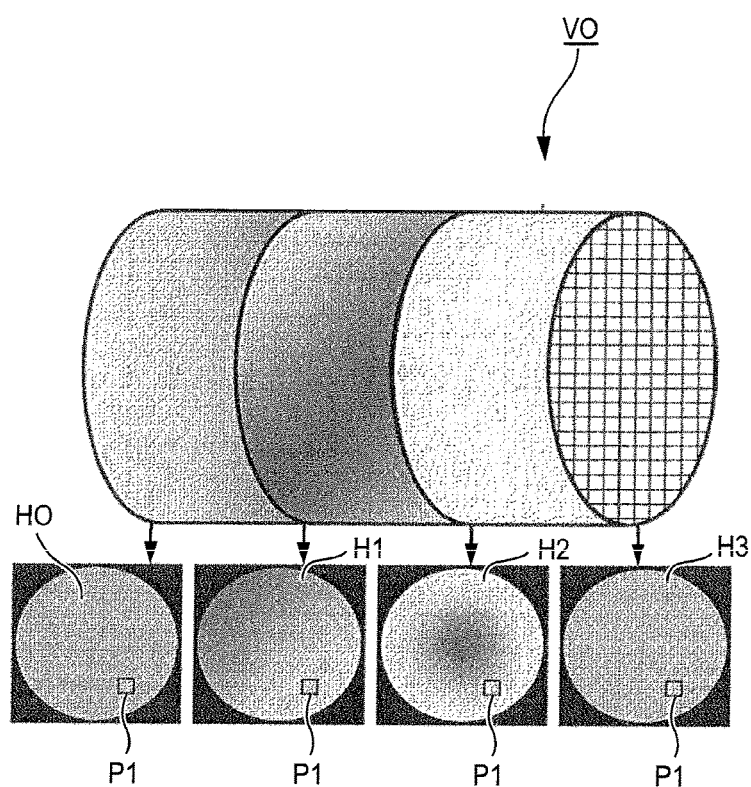
FIG. 20 is a diagram illustrating a correction amount calculating process performed in step ST13 of FIG. 12.

In step ST13, the boundary corrector 19 calculates the correction amount of the CT values in the boundary surfaces on the basis of the final CT value difference distributions H1 and H2. For example, the boundary corrector 19 determines the middle value of the CT value differences as the correction amount. The correction amount is set every plural pixels constituting the axial section image I1 or the axial section image I2. One pixel P1 shown in FIG. 20 will be paid attention to.

Figure 21:
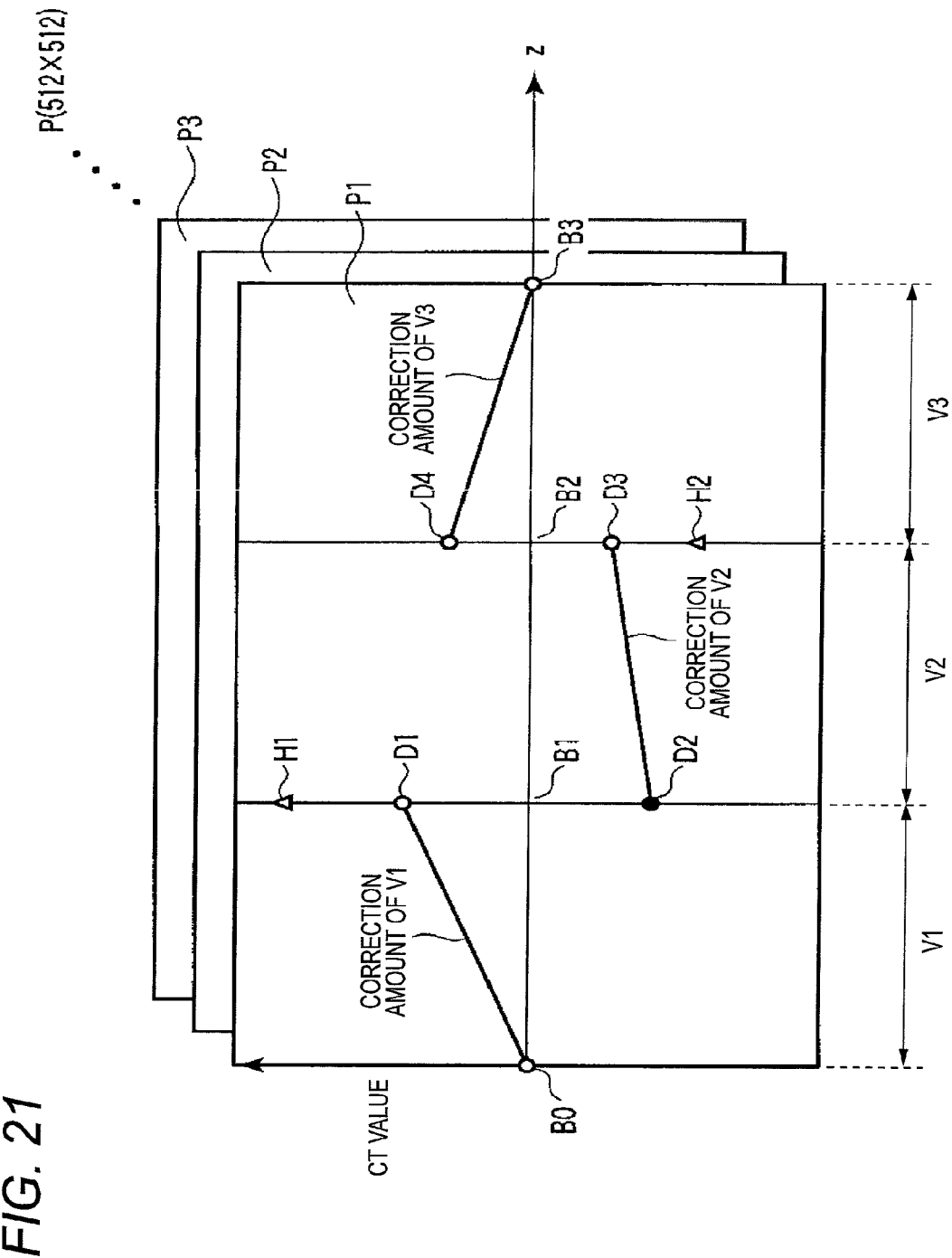
FIG. 21 is a diagram illustrating a graph of correction amounts calculated in step ST13 of FIG. 12.

FIG. 21 shows the CT value difference H1 of the boundary surface B1 and the CT value difference H2 of the boundary surface B2 for the pixel P1. The boundary corrector 19 determines a half value of the CT value difference H1 as the correction amount of the CT value of the boundary surface B1. Specifically, the boundary corrector 19 sets the correction amount D1 of the first volume data set V1 in the boundary surface B1 to +H1/2. The boundary corrector 19 sets the correction amount D2 of the second volume data set V2 in the boundary surface B1 to −H1/2. Similarly, the boundary corrector 19 sets the correction amount D3 of the second volume data set V2 in the boundary surface B2 to +H2/2. The boundary corrector 19 sets the correction amount D4 of the third volume data set V3 in the boundary surface B2 to −H2/2. In this way, the correction amounts of the volume data sets V1, V2, and V3 in the boundary surfaces are determined.

In the above description, the overlapping portion includes a single axial section image. However, the first embodiment is not limited to the configuration. For example, the overlapping portion may include plural axial section images arranged in the slice direction. In this case, the boundary corrector 19 performs the processes of steps ST11, ST12, and ST13 on the respective axial section images to determine the correction amounts of the axial section images included in the overlapping portion. Accordingly, the correction amounts of the overlapping portion are determined.

In step ST14, the boundary corrector 19 sets the correction amounts of the end surface B0 and the end surface B3 of the imaging area FOV (the synthesized volume data V0) to zero. In this way, as shown in FIG. 21, the correction amounts of the end surface B0, the end surface B3, the boundary surface B1, and the boundary surface B2 are determined.

In step ST15, the boundary corrector 19 calculates the correction amount of the CT values of the area (hereinafter, referred to as "non-overlapping portion") other than the boundary surfaces (overlapping portions) and the end surfaces in the volume data sets V1, V2, and V3. For example, as shown in FIG. 21, the boundary corrector 19 calculates the correction amounts of the plural pixels constituting the non-overlapping portion by the use of linear interpolation. Specifically, the boundary corrector 19 calculates the correction amounts of the non-overlapping portion from the correction amount "0" of the end surface B0 of the first volume data set V1 and the correction amount "D1" of the boundary surface B1 by the use of the linear interpolation. The calculation of the correction amount of the pixel P1 will be exemplified. The correction amount of the non-overlapping portion of the pixel P1 in the first volume data set V1 is defined by a straight line connecting the correction amount "0" of the end surface B0 to the correction amount "D1" of the boundary surface B1. Similarly, the correction amount of the non-overlapping portion of the pixel P1 in the second volume data set V2 is defined by a straight line connecting the correction amount "D2" of the boundary surface B1 to the correction amount "D3" of the boundary surface B2. Similarly, the correction amount of the non-overlapping portion of the pixel P1 in the third volume data set V3 is defined by a straight line connecting the correction amount "D4" of the boundary surface B2 to the correction amount "0" of the end surface B3. The boundary corrector 19 performs the above-mentioned process on all the N×N pixels to calculate the correction amounts of all the N×N pixels (P1, P2, . . . , P512×512).

In this way, the correction amounts (that is, the correction amount of the synthesized volume data set V0) of the first volume data set V1, the second volume data set V2, and the third volume data set V3 are determined.

The correction method is not limited to the above-mentioned method. For example, the boundary corrector 19 may replace the CT values of the respective axial section images with the average CT values of two axial section images.

Figure 22:
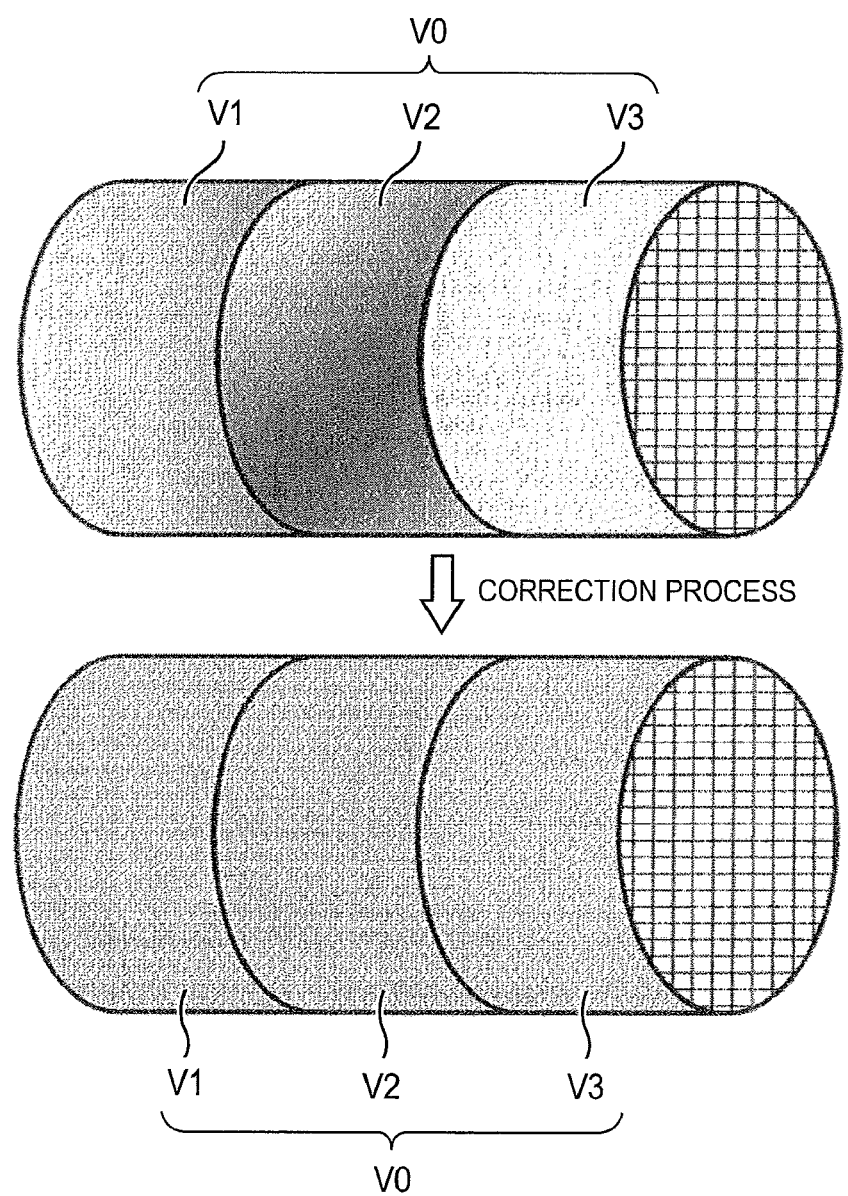
FIG. 22 is a diagram schematically illustrating the first volume data set, the second volume data set, and the third volume data set after being subjected to the boundary correcting process in step ST7 of FIG. 2.

In step ST16, the boundary corrector 19 corrects the CT values of the volume data set V1, the volume data set V2, and the volume data set V3 on the basis of the correction amounts determined in steps ST13, ST14, and ST15, as shown in FIG. 22. Accordingly, the CT values of the volume data set V1, the volume data set V2, and the volume data set V3 are smoothly continuous in space.

In this way, the boundary correcting process in the boundary corrector 19 is finished. In the above description, the boundary correcting process is performed on both the overlapping portion and the non-overlapping portion of each volume data set. However, the boundary correcting process is not limited to the above-mentioned configuration. For example, the boundary corrector 19 may perform the boundary correcting process only on the overlapping portion of each volume data set.

When the boundary correction process in the boundary corrector 19 is finished, the synthesizer 21 generates a synthesized volume data set on the basis of the first volume data set, the second volume data set, and the third volume data set having been subjected to the boundary correcting process.

The process of step ST7 is finished as described above.

When the process of step ST7 is finished, the image storage unit 22 stores the synthesized volume data set in step ST8, as shown in FIG. 2.

In step ST9, the image processor 23 performs various image processes on the volume data sets stored in the image storage unit 21 to generate a data set of a two-dimensional display image. Various setting conditions and areas of interest at the time of generating the display image are set on the basis of the operator's input to the input unit 14.

In step ST10, the display unit 24 displays the display image generated by the image processor 23.

When the process of step ST10 is performed, the operation of the X-ray CT scanner 1 is ended.

The sequence of processes is not limited to the flow shown in FIG. 2. For example, the boundary correcting process may be performed after the synthesis process, or the synthesis process may be performed after the boundary correcting process.

According to the first embodiment, the X-ray CT scanner 1 can reduce the discontinuity of the CT values between the volume data sets due to the variation of the X-ray energy in the slice direction (cone-angle direction) by the use of the above-mentioned boundary correcting process. The X-ray CT scanner 1 can improve the spatial continuity of CT values between the adjacent volume data sets. The X-ray CT scanner 1 can reduce the differences in CT value between both ends of the volume area. The X-ray CT scanner 1 can easily calculate the correction amounts in the boundary correcting process by causing the adjacent volume data sets to overlap with each other.

Second Embodiment

A second embodiment of the invention will be described below. The second embodiment is different from the first embodiment, in the shape of a scan area (the shape of a volume data set) and the boundary correcting process. Accordingly, only the shape of the scan areas and the boundary correcting process according to the second embodiment will be described below.

Figure 23:
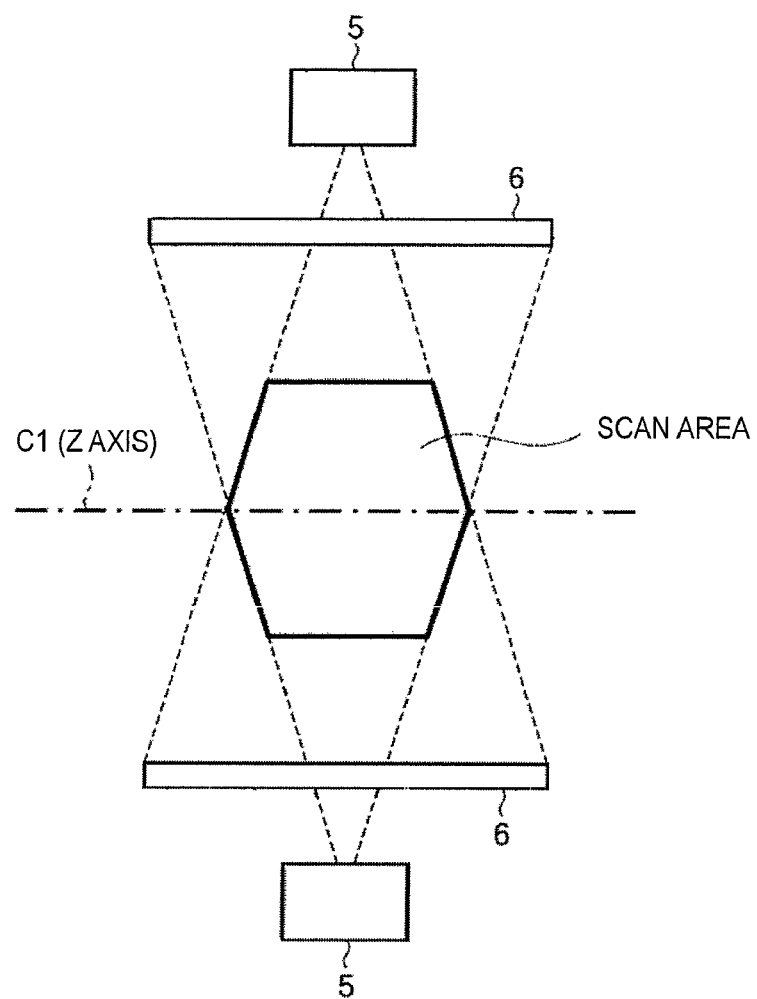
FIG. 23 is a diagram illustrating a scan area according to a second embodiment of the invention.

As shown in FIG. 23, the shape of the scan area according to the second embodiment is set to a shape obtained by rotating a pedestal shape about the bottom. The scan area according to the second embodiment includes a cylindrical portion and a conic portion. The conic portion is derived from the area in the cone-angle direction of the radiated X-ray. Inside the conic portion, since the projection data sets sufficient for reconstruction are collected, an image deterioration does not occur. However, outside the conic portion, since the projection data sets for reconstruction are not collected, the image deterioration occurs. The shape of the scan area according to the first embodiment is set to a cylindrical shape as shown in FIG. 8.

Figure 24:
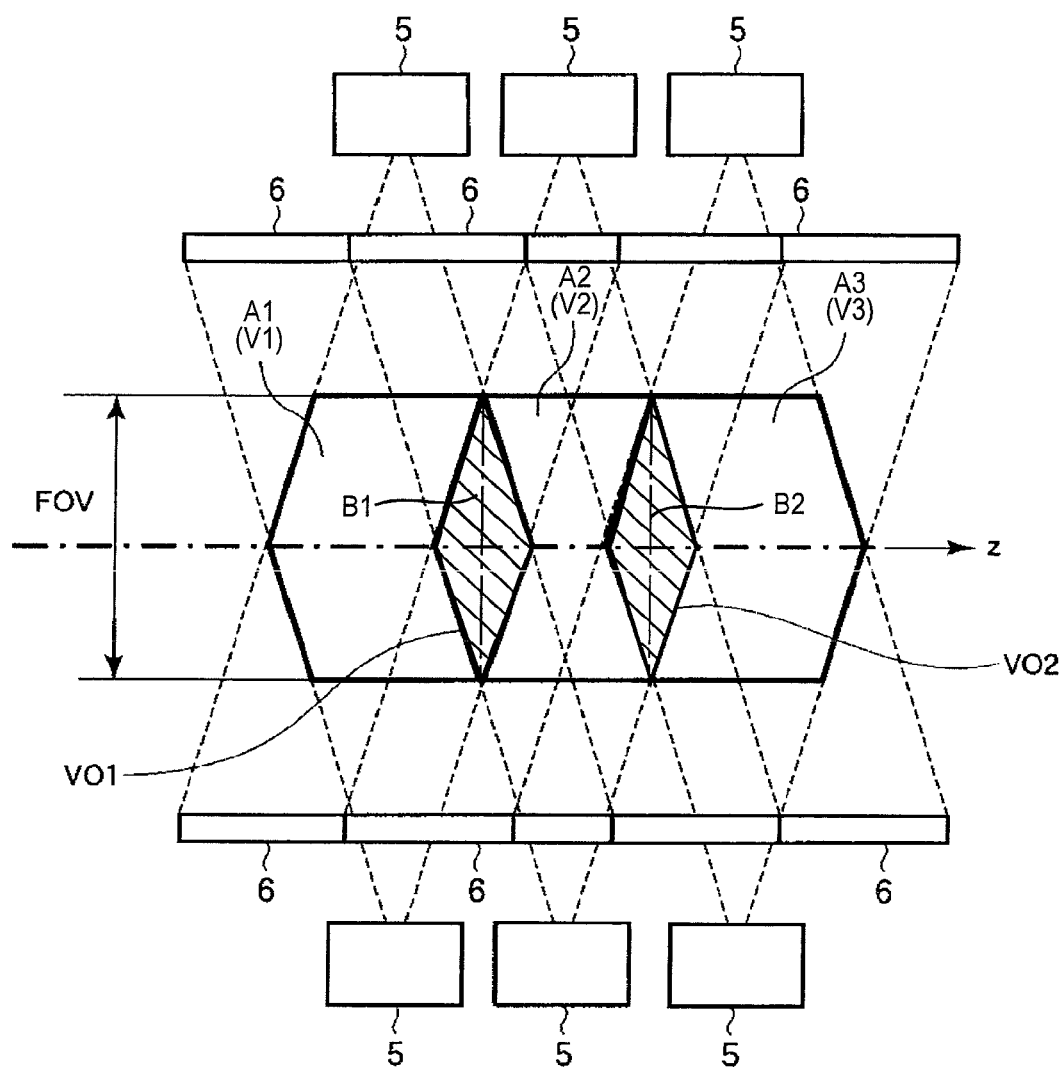
FIG. 24 is a diagram illustrating a positional relation of a first scan area, a second scan area, and a third scan area according to the second embodiment.

In the second embodiment, as shown in FIG. 24, a first scan area A1 and a second scan area A2 overlap with each other. Specifically, the first scan area A1 and the second scan area A2 are positioned so that at least one axial section in the boundary surface B1 in the cylindrical portion overlaps and the entire conic portion overlaps. Similarly, the second scan area A2 and a third scan area A3 are positioned so that at least one axial section in the boundary surface B2 in the cylindrical portion overlaps and the entire conic portion overlaps. That is, more axial sections than those in the first embodiment overlap.

The boundary correcting process in the boundary corrector 19 according to the second embodiment will be described.

Figure 25:
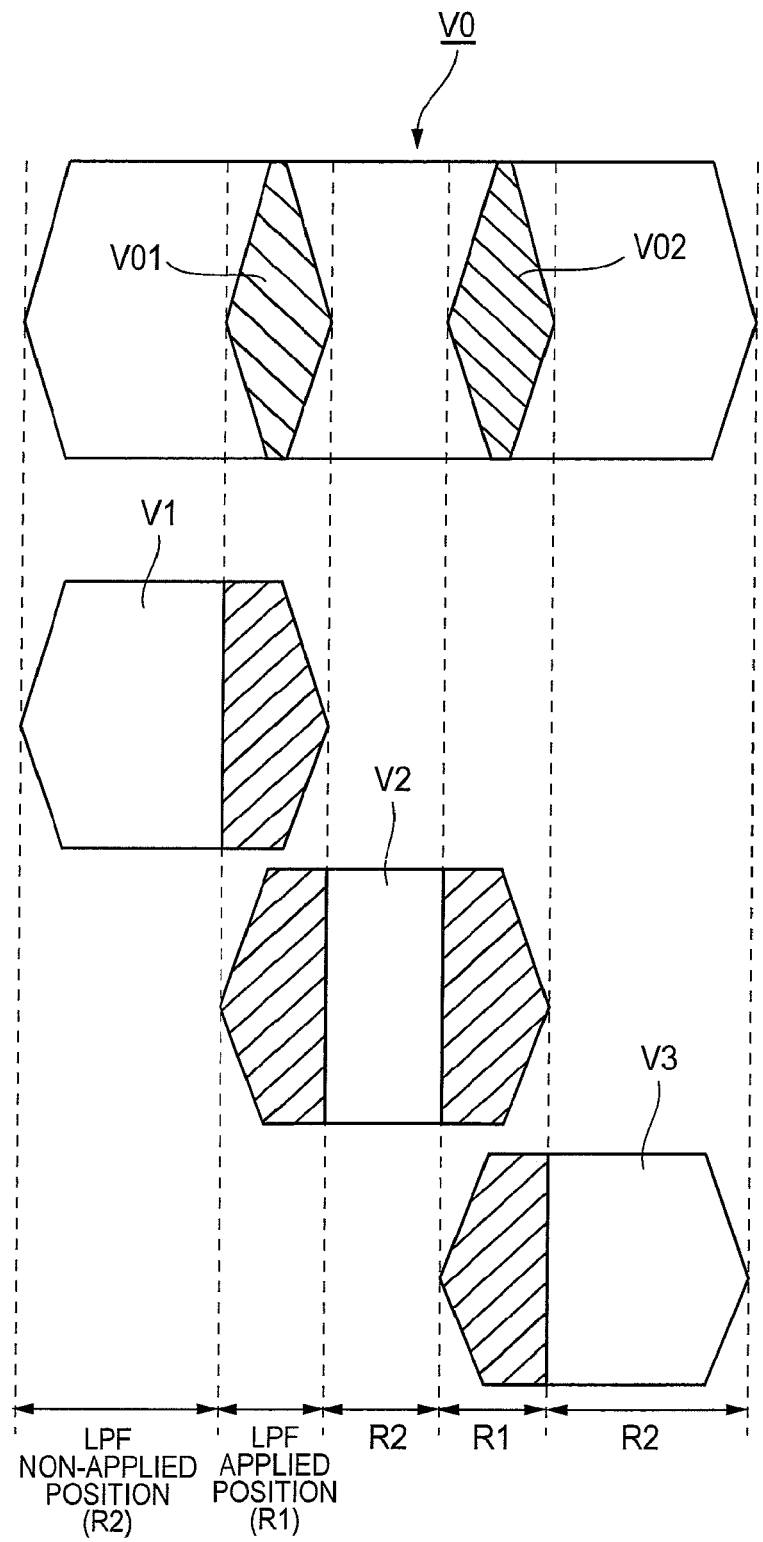
FIG. 25 is a diagram illustrating portions on which a high-frequency component removing or reducing process is performed by a boundary corrector according to the second embodiment.

The boundary corrector 19 removes or reduces the high-frequency component included in each volume data set by the use of the low-pass filter (LPF) before step ST11 of the boundary correcting process. FIG. 25 is a diagram schematically illustrating an applied region R1 to which the low-pass filter is applied and a non-applied region R2 to which the low-pass filter is not applied. As shown in FIG. 25, the applied region R1 is all the axial section images including the overlapping portion VO. In other words, the applied region R1 is an end portion in the slice direction of each volume data set. By applying the low-pass filter, the high-frequency component included in the CT value difference distribution is reduced, thereby improving the correction precision of the boundary correcting process. The application of the low-pass filter may be performed before step ST11 in the first embodiment.

In step ST11, the boundary corrector 19 generates the CT value difference distribution from two axial section images of the overlapping axial sections. The boundary corrector 19 generates the CT value difference distribution every axial section included in the overlapping portion.

In step ST12, the boundary corrector 19 generates the final CT value difference distribution by removing the high-frequency component from the CT value difference distribution.

Figure 26:
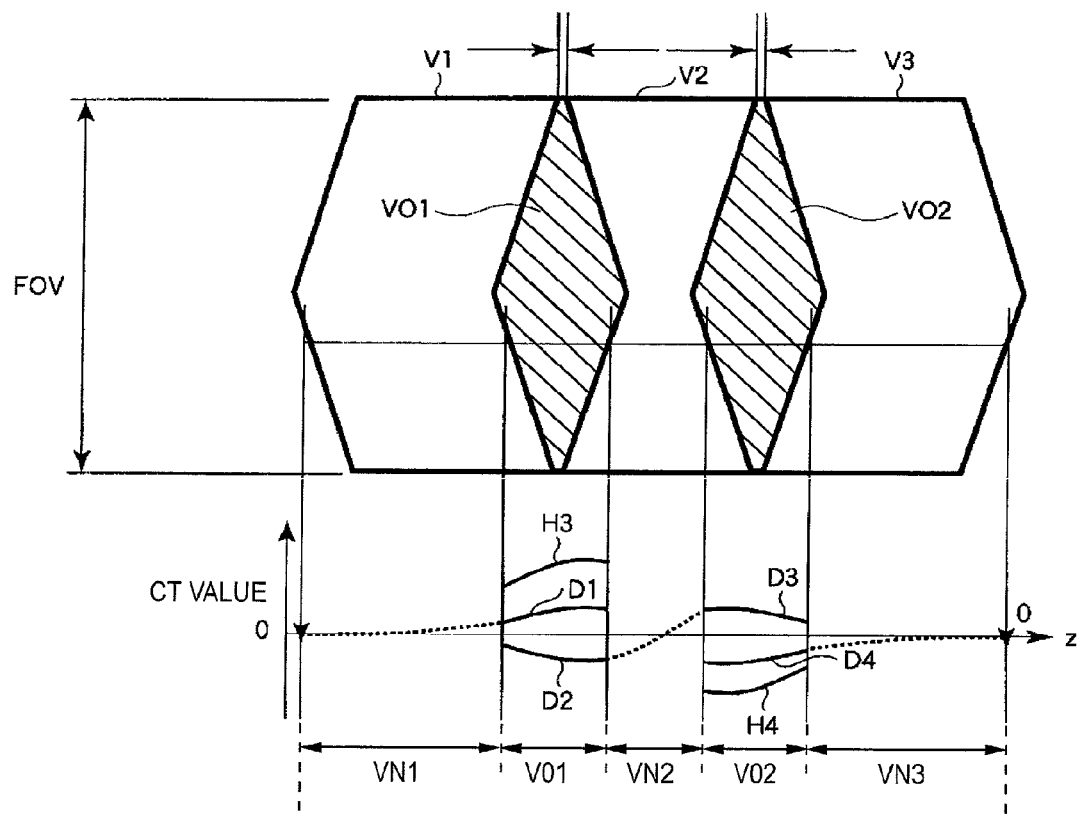
FIG. 26 is a diagram illustrating a boundary correcting process performed by the boundary corrector according to the second embodiment.

As shown in FIG. 26, paying attention to the pixel P1, a CT value difference curve H3 is obtained in the overlapping portion VO1 and a CT value difference curve H4 is obtained in the overlapping portion VO2. The CT value difference curve represents the variation in CT value difference depending on positions in the slice direction. The CT value difference curve H3 and the CT value difference curve H4 smoothly increase or decrease in the slice direction.

In step ST13, the boundary corrector 19 calculates the correction amount "D1" of the overlapping portion VO1 of the volume data set V1 and the correction amount "D2" of the volume data set V2 on the basis of the half value of the CT value difference curve H3. Similarly, the boundary corrector 19 calculates the correction amount "D3" of the overlapping portion VO2 of the volume data set V2 and the correction amount "D4" of the overlapping portion VO2 of the volume data set V3 on the basis of the half value of the CT value difference curve H4. Similarly to the first embodiment, numerical expressions H3=I1−I2, H4=I2−I3, D1=+H3/2, D2=−H3/2, D3=+H4/2, and D4=−H4/2 can be used.

In step ST14, the boundary corrector 19 determines the correction amount in the end surface B0 of the synthesized volume data set V0 and the correction amount in the end surface B3 to zero. In this way, the correction amounts in both end surfaces of the synthesized volume data set V0 and the correction amount in the overlapping portion are determined.

In step ST15, the boundary corrector 19 calculates the correction amount of the non-overlap portion of the volume data set. For example, as shown in FIG. 26, the boundary corrector 19 calculates the correction amounts of the non-overlapping portion VN1 of the first volume data set V1, the non-overlapping portion VN2 of the second volume data set V2, and the non-overlapping portion VN3 of the third volume data set V3 by the use of nonlinear interpolation. Specifically, the correction amount of the pixel P1 in the non-overlapping portion VN1 is calculated from the correction amount "0" of an end surface of the first volume data set V1 and the correction amount "D1" of the other end surface by the use of the nonlinear interpolation. The nonlinear interpolation is based on a polygonal approximation such as a sine function, a cosine function, and a spline function. Similarly, the boundary corrector 19 calculates the correction amount of the pixel P1 in the non-overlapping portion VN2 from the correction amount of the boundary surface close to V1 in the second volume data set V2 and the correction amount of the boundary surface close to V3 by the use of the nonlinear interpolation. The boundary corrector 19 calculates the correction amount of the pixel P1 in the non-overlapping portion VN3 from the correction amount of the boundary surface close to V2 in the third volume data set V3 and the correction amount "0" of the end surface by the use of the nonlinear interpolation.

The boundary corrector 19 performs the correction amount calculating process described with reference to the pixel P1 on all the N×N pixels. Accordingly, the correction amounts of the entire synthesized volume data set V0 are determined.

In step ST16, the boundary corrector 19 corrects the CT values of the first volume data set V1, the second volume data set V2, and the third volume data set V3 on the basis of the correction amounts determined in steps ST13, ST14, and ST15. In this way, the boundary correcting process is finished. By this boundary correcting process, the spatial continuity of the CT values in the synthesized volume data set V0 is improved.

As described above, the same advantages as the first embodiment can be obtained in the second embodiment. The overlapping portion in the second embodiment is greater than the overlapping portion in the first embodiment. Accordingly, the X-ray CT scanner 1 according to the second embodiment can more smoothly vary the CT values between the volume data sets than the X-ray CT scanner according to the first embodiment.

Third Embodiment

A third embodiment of the invention will be described below. The boundary corrector 19 according to the third embodiment performs the boundary correcting process on projection data sets. The third embodiment is different from the first embodiment, only in the boundary correcting process. Therefore, only the boundary correcting process in the third embodiment will be described.

Figure 27:
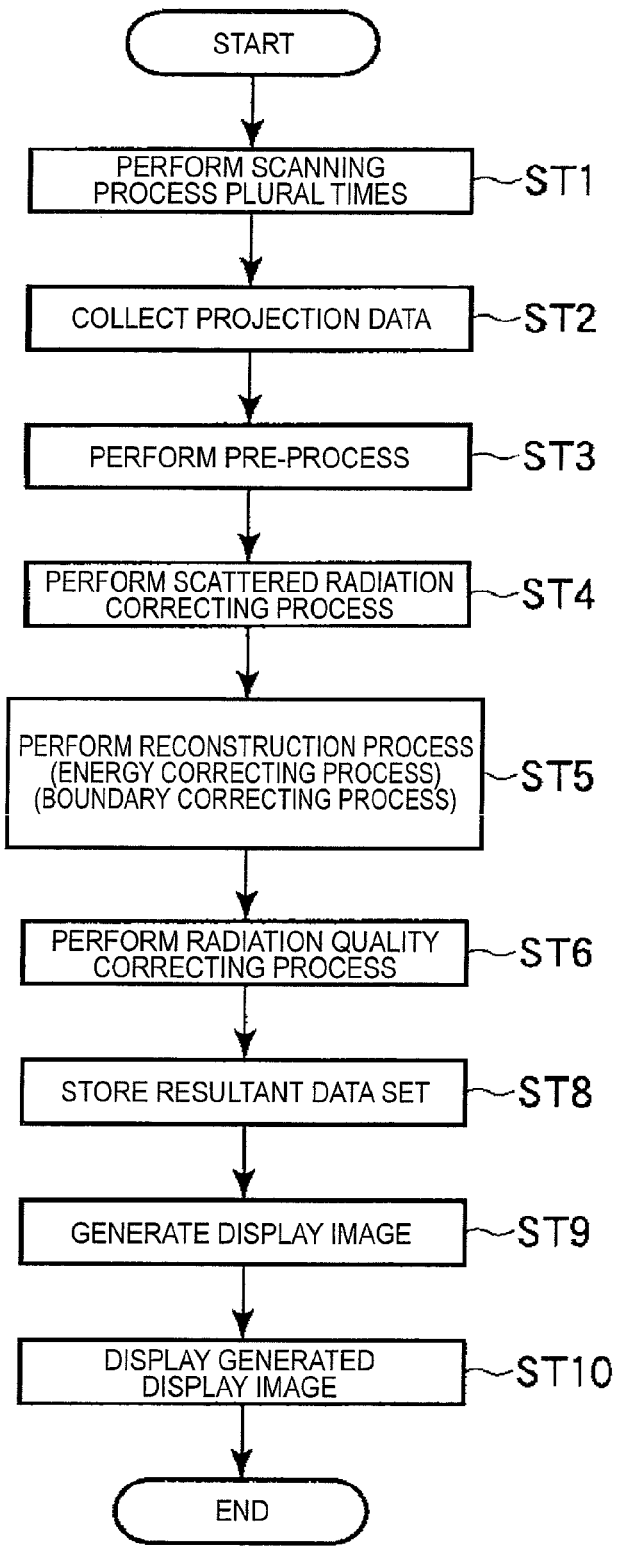
FIG. 27 is a diagram illustrating a typical flow of operations in an X-ray CT scanner according to a third embodiment of the invention.

In the third embodiment, as shown in FIG. 27, the boundary correcting process in the boundary corrector 19 is included in the reconstruction process in the reconstruction processor 17. For example, the boundary corrector 19 performs a weighting process on the projection data sets collected by plural times of circular orbital scans at the time of performing the reconstruction process in step ST5. The reconstruction processor 17 performs an added average process on the projection data sets having been subjected to the weight process.

An example where a projection data set (hereinafter, referred to as "first projection data set") of the first scan area and a projection data set (hereinafter, referred to as "second projection data set") of the second scan area should be subjected to the boundary correcting process will be described below. The first scan area and the second scan area include the same anatomic overlapping portion. In other words, the first projection data set includes a component of an axial section (hereinafter, referred to as "overlapping section component") in an overlapping portion and a component of an axial section (hereinafter, referred to as "non-overlapping section component") in a non-overlapping portion. Similarly, the second projection data set includes the overlapping section component and the non-overlapping section component. The overlapping section component of the first projection data and the overlapping section component of the second projection data set are derived from the same anatomic overlapping portion.

For example, it is assumed that plural axial sections of the overlapping portion in the first scan area and plural axial sections of the overlapping portion in the second scan area overlap with each other. Here, among the axial sections included in the overlapping portion, the axial section closest to the center of the first scan area is called first axial section, the axial section located at the center of the overlapping portion is called center axial section, and the axial section closest to the center of the second scan area is called second axial section.

For example, the boundary corrector 19 applies a weight "90%" to the overlapping section component of the first axial section of the first projection data and applies a weight "10%" to the overlapping section component of the first axial section of the second projection data set. The boundary corrector 19 applies a weight "50%" to the overlapping section component of the center axial section of the first projection data and applies a weight "50%" to the overlapping section component of the center axial section of the second projection data set. The boundary corrector 19 applies a weight "10%" to the overlapping section component of the second axial section of the first projection data and applies a weight "90%" to the overlapping section component of the second axial section of the second projection data set.

The same advantages as the first embodiment and the second embodiment can be obtained in the third embodiment. The X-ray CT scanner 1 according to the third embodiment can more reduce the processing load or the processing time of the boundary correcting process than the X-ray CT scanner 1 according to the first embodiment or the X-ray CT scanner 1 according to the second embodiment, by correcting the boundaries at the time of performing the reconstruction process.

Fourth Embodiment

The boundary corrector 19 according to a fourth embodiment of the invention performs the boundary correcting process based on a weighting process on the volume data sets. The boundary correcting process in the fourth embodiment will be described below. The fourth embodiment is different from the first embodiment, only in the process details of the boundary correcting process. Therefore, only the boundary correcting process in the fourth embodiment will be described.

An example where the first volume data set, the second volume data set, and the third volume data set should be subjected to the boundary correcting process will be described. The first volume data set and the second volume data set both include an overlapping portion. The second volume data set and the third volume data set also share an overlapping portion. The first volume data set, the second volume data set, and the third volume data set each include an overlapping portion and a non-overlapping portion. The overlapping portion of the first volume data set and the overlapping portion of the second volume data set correspond to the same anatomic overlapping portion. The overlapping portion of the second volume data set and the overlapping portion of the third volume data set correspond to the same anatomic overlapping portion.

Figure 28:
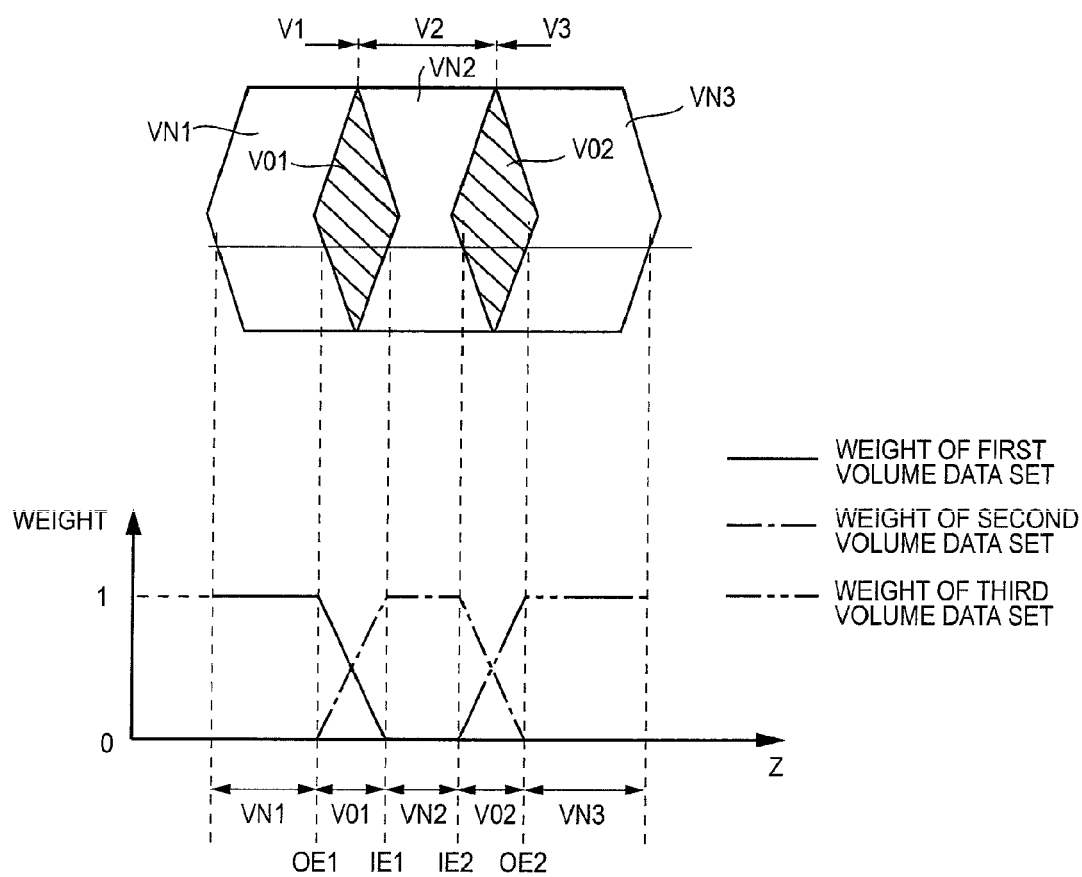
FIG. 28 is a diagram illustrating an example of weights in a weighting process performed by the boundary corrector according to a fourth embodiment of the invention.

FIG. 28 is a diagram illustrating an example of weights used in the weighting process in the boundary corrector 19. As shown in FIG. 28, the boundary corrector 19 multiplies the CT values of the non-overlapping portion VN1 of the first volume data set V1, the CT values of the non-overlapping portion VN2 of the second volume data set V2, and the CT values of the non-overlapping portion VN3 of the third volume data set V3 by a weight "1". That is, the boundary corrector 19 does not vary the CT values of the non-overlapping portion VN1, the CT values of the non-overlapping portion VN2, and the CT values of the non-overlapping portion VN3.

As shown in FIG. 28, the boundary corrector 19 multiplies the overlapping portions by a weight which is different depending on the positions in the Z axis direction. Specifically, the boundary corrector 19 multiplies the CT values of the overlapping portion VO1 of the first volume data set V1 and the second volume data set V2 by a linear weight. The boundary corrector 19 multiplies the CT values of the overlapping portion VO2 of the second volume data set V2 and the third volume data set V3 by a linear weight. The weighting process on the overlapping portion will be specifically described with reference to the overlapping portion VO1 and the overlapping portion VO2 of the second volume data set V2. The weight of the first overlapping portion VO1 of the second volume data set is "0" at an end (hereinafter, referred to as "first outer end") OE1 close to the non-overlapping portion VN1 and is "1" at the other end (hereinafter, referred to as "first inner end") IE1. The weight of the first overlapping portion VO1 of the second volume data set V2 between the first outer end OE1 and the first inner end IE1 is determined by the linear interpolation based on the weight "0" at the first outer end OE1 and the weight "1" at the first inner end IE1. Similarly, the weight of the overlapping portion VO2 of the second volume data set V2 is "0" at an end (hereinafter, referred to as "second outer end") OE2 close to the non-overlapping portion VN3 and is "1" at the other end (hereinafter, referred to as "second inner end") IE2. The weight of the second overlapping portion of the second volume data set V2 between the second outer end OE2 and the second inner end IE2 is determined by the linear interpolation based on the weight "0" at the second outer end OE2 and the weight "1" at the second inner end IE2.

Similarly, the weight of the overlapping portion VO1 of the first volume data set V1 and the weight of the overlapping portion VO2 of the third volume data set V3 are determined on the basis of the linear interpolation. The weights of the volume data sets V1, V2, and V3 are determined so that the total sum of the weights at the same position in the Z axis direction becomes "0".

Figure 29:
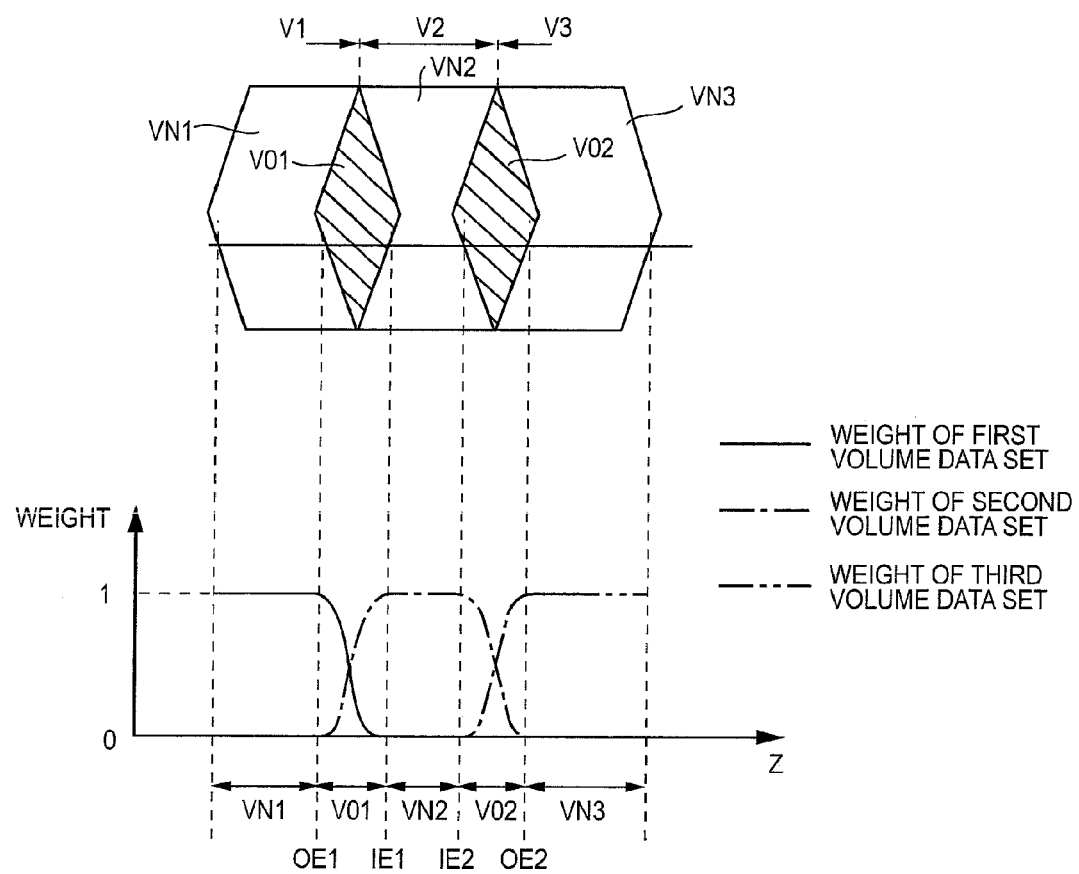
FIG. 29 is a diagram illustrating another example of weights in the weighting process performed by the boundary corrector according to the fourth embodiment of the invention.

FIG. 29 is a diagram illustrating another example of the weights used in the weight process in the boundary corrector 19. As shown in FIG. 29, the boundary corrector 19 multiplies the CT values of the non-overlapping portion VN1 of the first volume data set V1, the CT values of the non-overlapping portion VN2 of the second volume data set V2, and the CT values of the non-overlapping portion VN3 of the third volume data set V3 by a weight "1". The boundary corrector 19 multiplies the CT values of the overlapping portion VO1 of the first volume data set V1 and the second volume data set V2 by a nonlinear weight. The boundary corrector 19 multiplies the CT values of the overlapping portion VO2 of the second volume data set V2 and the third volume data set V3 by a nonlinear weight. For example, the weight of the first overlapping portion VO1 of the second volume data set V2 is "0" at the first outer end OE1 and is "1" at the first inner end IE1. The weight of the first overlapping portion VO1 of the second volume data set V2 between the first outer end OE1 and the first inner end IE1 is determined by the nonlinear interpolation based on the weight "0" at the first outer end OE1 and the weight "1" at the first inner end IE1. The nonlinear interpolation is based on a polygonal approximation such as a sine function, a cosine function, and a spline function. Similarly, the weight of the overlapping portion VO2 of the second volume data set V2 is "0" at the second outer end OE2 and is "1" at the second inner end IE2. The weight of the second overlapping portion VO2 of the second volume data set V2 between the second outer end OE2 and the second inner end IE2 is determined by the nonlinear interpolation based on the weight "0" at the second outer end OE2 and the weight "1" at the second inner end IE2.

Similarly, the weight of the overlapping portion VO1 of the second volume data set V2 and the overlapping portion VO2 of the third volume data set V3 are determined by the nonlinear interpolation. The weights of the volume data sets V1, V2, and V3 are determined so that the total sum of the weights at the same position in the Z axis direction becomes "0".

When the CT values of the overlapping portion VO1 of the first volume data set V1, the CT values of the overlapping portion VO1 of the second volume data set V2, the CT values of the overlapping portion VO2 of the second volume data set V2, and the CT values of the overlapping portion VO2 of the third volume data set V3 are multiplied by the linear weights shown in FIG. 28 or the nonlinear weights shown in FIG. 29, the synthesizer 21 adds the CT values of the first volume data set V1, the CT values of the second volume data set V2, and the CT values of the third volume data set V3, which are multiplied by the weights. The synthesizer 21 generates the synthesized volume data set by this addition process.

The method of determining a weight of an overlapping portion is not limited to the above-mentioned method. For example, it may be considered that the volume data set has a shape obtained by combining a cylindrical shape and a conic shape. It is assumed that the conic portions and the cylindrical portions of two volume data sets partially overlap. That is, the overlapping portion includes two conic portions and one cylindrical portion.

Figure 30:
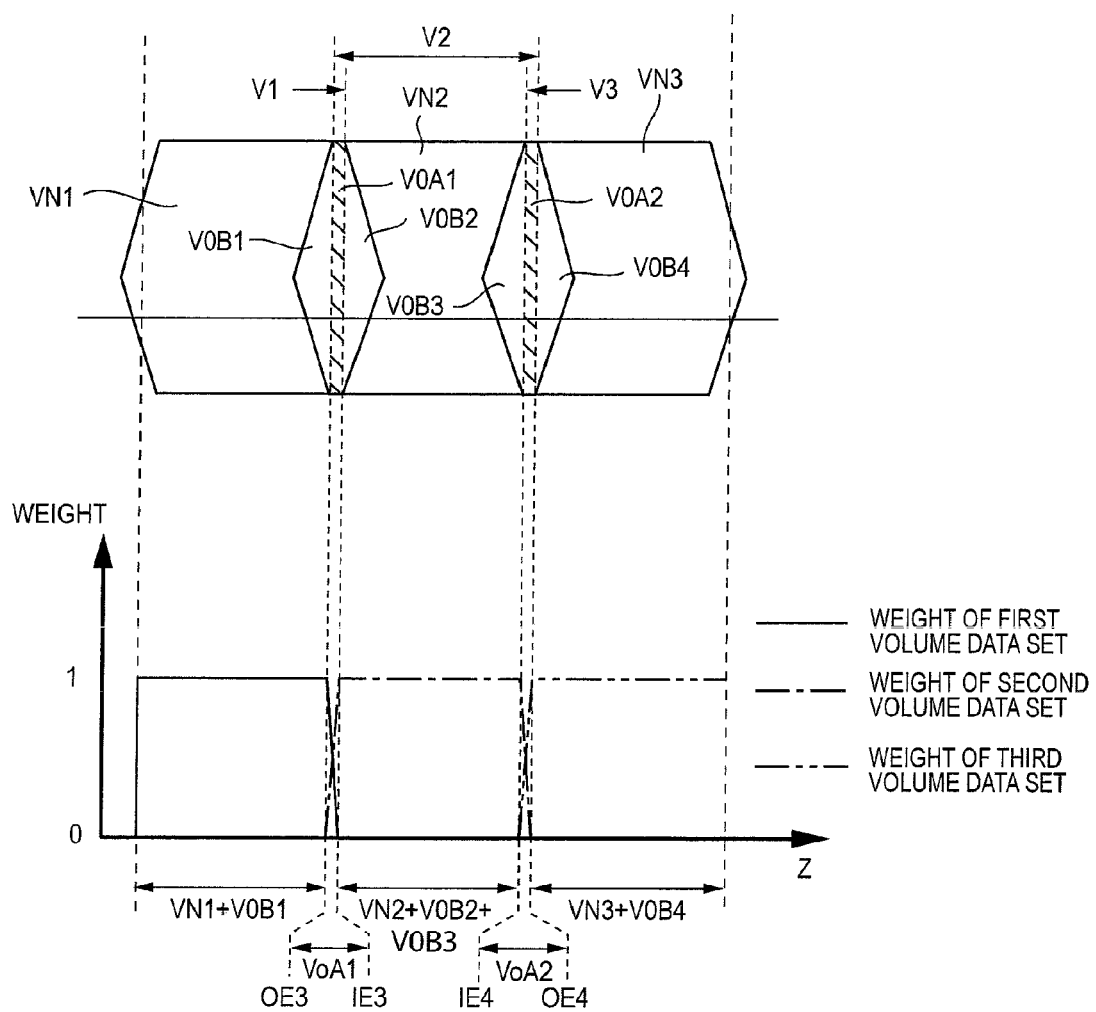
FIG. 30 is a diagram illustrating another example of weights in the weighting process performed by the boundary corrector according to the fourth embodiment of the invention.

In this case, the boundary corrector 19 determines the weight of the cylindrical portion in the overlapping portion by the linear interpolation or the nonlinear interpolation. An example where the weight of the cylindrical portion VOA in the overlapping portion VO is determined will be described with reference to FIG. 30. It is assumed that the weight is determined by the linear interpolation. As shown in FIG. 30, the overlapping portion of the first volume data set and the second volume data set includes a cylindrical portion VOA1, a conic portion VOB1, and a conic portion VOB2. Similarly, the overlapping portion of the second volume data set and the third volume data set includes a cylindrical portion VOA2, a conic portion VOB3, and a conic portion VOB4.

As shown in FIG. 30, the boundary corrector 19 multiplies CT values of a non-overlapping portion VN of a volume data set to be processed by the weight "1". The boundary corrector 19 multiplies the CT values of the conic portion VOB close to the non-overlapping portion VN of the volume data set among the conic portions VOB of the volume data set to be processed by the weight "1". Specifically, the boundary corrector 19 multiplies the non-overlapping portion VN1 and the conic portion VOB1 of the first volume data set V1 by the weight "1". The boundary corrector 19 multiplies the non-overlapping portion VN2, the conic portion VOB2, and the conic portion VOB3 of the second volume data set V2 by the weight "1". The boundary corrector 19 multiplies the non-overlapping portion VN3 and the conic portion VOB4 of the third volume data set V3 by the weight "1".

As shown in FIG. 30, the boundary corrector 19 multiplies the CT values of the cylindrical portion VOA of a volume data set to be processed by the weight based on the linear interpolation. For example, the weight of the cylindrical portion VOA1 of the second volume data set V2 is "0" at an end (hereinafter, referred to as "third outer end") OE3 close to the non-overlapping portion VN1 and is "1" at the other end (hereinafter, referred to as "third inner end") IE3. The weight of the cylindrical portion VOA1 of the second volume data set V2 between the third outer end OE3 and the third inner end IE3 is determined by the linear interpolation based on the weight "0" at the third outer end OE3 and the weight "1" at the third inner end IE3. Similarly, the weight of the cylindrical portion VOA2 of the second volume data set V2 is "0" at an end (hereinafter, referred to as "fourth outer end") OE4 close to the non-overlapping portion VN3 and is "1" at the other end (hereinafter, referred to as "fourth inner end") IE4. The weight of the second cylindrical portion VOA2 of the second volume data set V2 between the fourth outer end OE4 and the fourth inner end IE4 is determined by the linear interpolation based on the weight "0" at the fourth outer end OE4 and the weight "1" at the fourth inner end IE4.

Similarly, the weight of the cylindrical portion VOA1 of the first volume data set V1 and the weight of the cylindrical portion VOA2 of the third volume data set V3 are determined by the linear interpolation. The weights of the volume data sets V1, V2, and V3 are determined so that the total sum of the weights at the same position in the Z axis direction becomes "0".

The same advantages as the first embodiment can be obtained in the fourth embodiment. It is possible to reduce the processing load and the processing time by performing the boundary correcting process on the basis of the weighting process.

The invention is not limited to the above-mentioned embodiments, but may be modified in various forms without departing from the spirit and scope of the invention at the time of putting the invention into practice.

Modified Example 1

In the above-mentioned embodiment, the boundary corrector 19 performs the boundary correcting process on two volume data sets overlapping with each other. However, the invention is not limited to the embodiment. For example, the boundary corrector 19 according to Modified Example 1 may perform the boundary correcting process on two volume data sets adjacent to each other. The "adjacent" means that two volume data sets overlap with each other with a gap smaller than a slice pitch (a spatial resolution in the Z axis direction of the volume data sets).

That is, the boundary corrector 19 calculates the correction amount on the basis of the CT value differences between the axial section image at an end of a volume data set (for example, the first volume data set) and the axial section image at an end of another volume data set (for example, the second volume data set).

Modified Example 2

Figure 31:
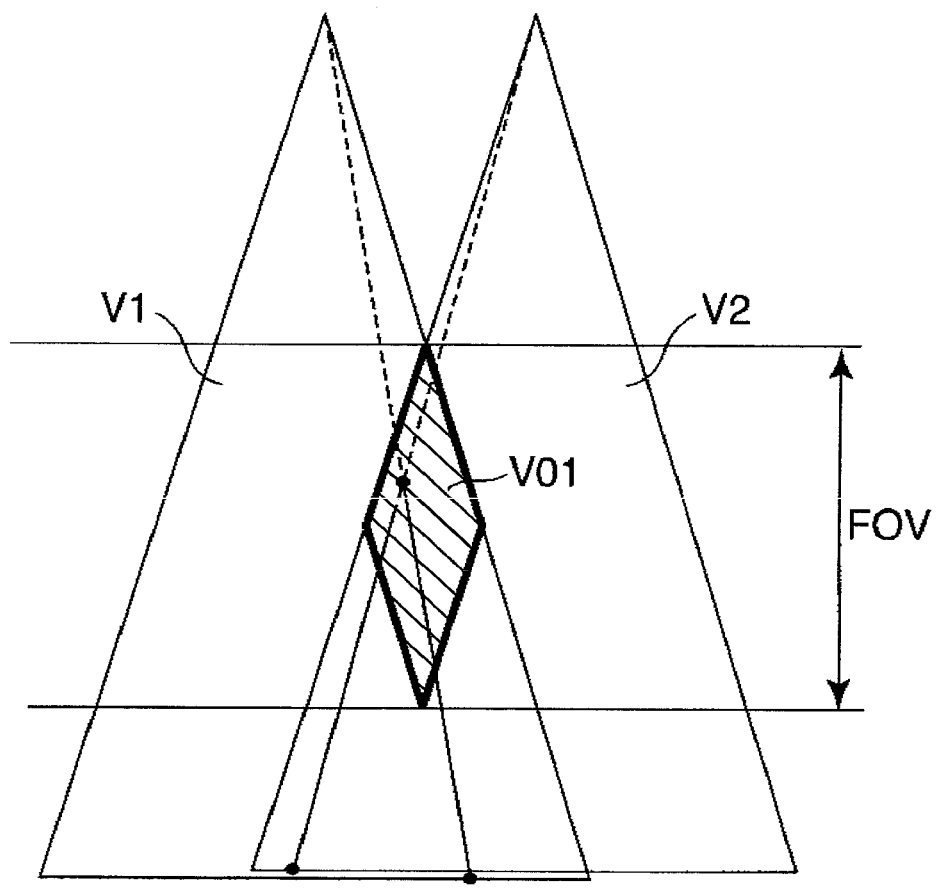
FIG. 31 is a diagram illustrating a reconstruction process performed by a reconstruction processor according to Modified Example 2 of the invention.

The reconstruction processor 17 according to Modified Example 2 may use the projection data of plural X-ray passes adjacent to the overlapping portion as well as the projection data of the X-ray pass passing through the overlapping portion, in reconstructing the overlapping portion. For example, as shown in FIG. 31, a case can be considered where the axial section image of the overlapping portion VO1 of the first volume data set V1 and the second volume data set V2 is reconstructed. The reconstruction processor 17 according to Modified Example 2 reconstructs the axial section image of the overlapping portion VO1 on the basis of the projection data of the X-ray pass passing through the overlapping portion VO1 and the projection data of the X-ray passes adjacent to the overlapping portion. At this time, the reconstruction processor 17 may project back the projection data of the overlapping portion VO1 and may multiply the projection data by the weight varying linearly or nonlinearly depending on the positions in the Z axis direction.

Modified Example 3

The X-ray CT scanner 1 according to the above-mentioned embodiments performs three types of correction processes of the scattered radiation correction, the X-ray energy correction, and the radiation quality correction. However, the invention is not limited to the embodiments. The X-ray CT scanner 1 according to Modified Example 3 may skip one or more of three correction processes.

Modified Example 4

Figure 32:
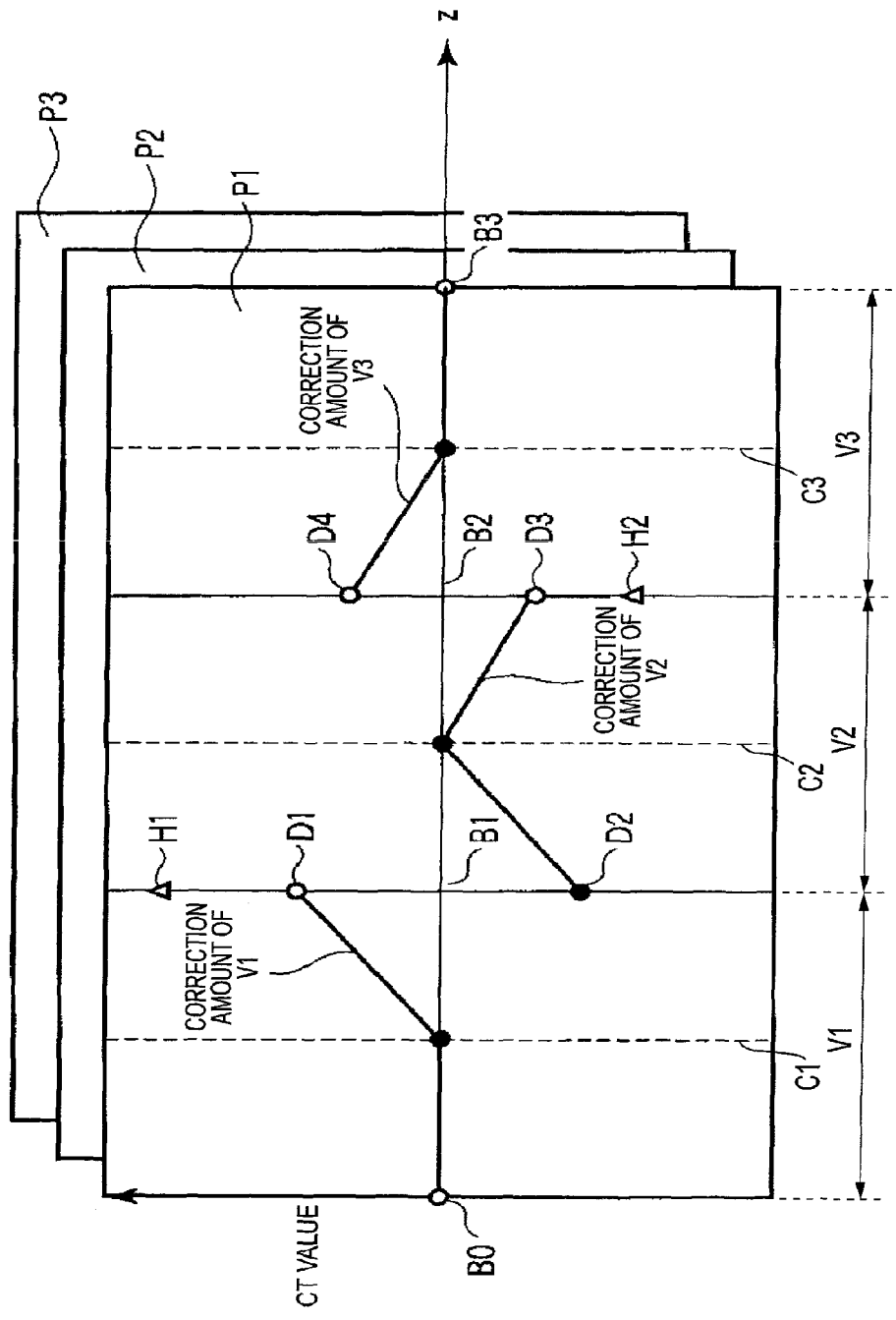
FIG. 32 is a diagram illustrating a graph of correction amounts calculated by a boundary corrector according to Modified Example 4 of the invention.

The boundary corrector 19 according to Modified Example 4 determines zero as the correction amounts of the center positions C1, C2, and C3 in the Z axis direction of the volume data sets V1, V2, and V3 at the time of calculating the correction amount of the non-overlapping portion, as shown in FIG. 32. In other words, the boundary corrector 19 determines zero as the correction amounts of the pixels located right below the X-ray focus on the anode 5a. The boundary corrector 19 calculates the correction amount between the boundary surface and the center position from the correction amount of the boundary surface and the correction amount of the center position by the use of the linear interpolation. At this time, the nonlinear interpolation may be used instead of the linear interpolation.

Modified Example 5

Figure 33:
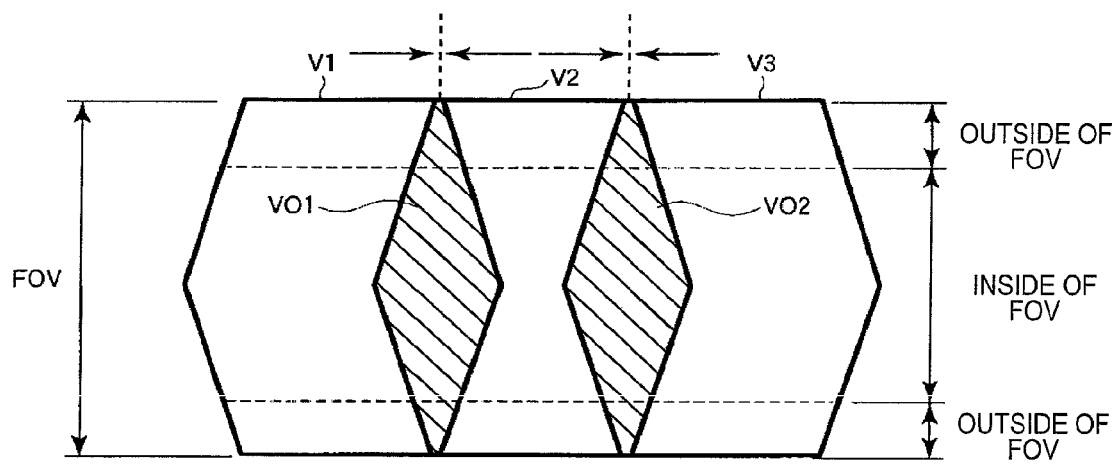
FIG. 33 is a diagram illustrating a boundary correcting process performed by a boundary corrector according to Modified Example 5 of the invention.

The boundary corrector 19 according to Modified Example 5 may calculate the correction amounts by combination of the linear interpolation and the nonlinear interpolation. For example, as shown in FIG. 33, a case will be described where an end portion in the slice direction of the imaging area FOV has a conic shape. The boundary corrector 19 selectively uses the linear interpolation and the nonlinear interpolation depending on the positions of a non-overlapping portion to be calculated, at the time of calculating the correction amount of the non-overlapping portion on the basis of the correction amount of the boundary surface. For example, the boundary corrector 19 calculates the correction amount of the outside of the imaging area FOV about the XY plane by the use of the linear interpolation, and calculates the inside of the imaging area FOV about the XY plane by the use of the nonlinear interpolation. For example, a trend curve can be used in the nonlinear interpolation. That is, the boundary corrector 19 uses the linear interpolation for the portion having a small amount of overlap, such as the outside, and uses the nonlinear interpolation for a portion having a great amount of overlap, such as the inside. Accordingly, the X-ray CT scanner 1 can perform an appropriate correction process depending on the amount of overlap.

Modified Example 6

Figure 34:
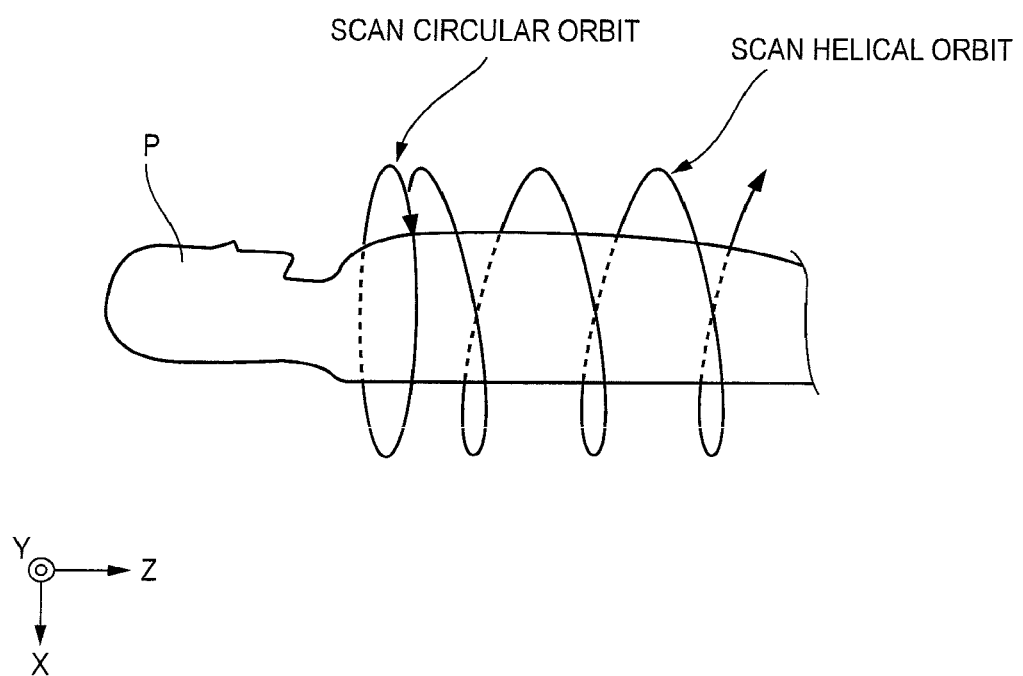
FIG. 34 is a diagram illustrating a positional relation of a circular orbital scan and a helical scan performed by a console controller according to Modified Example 6 of the invention.

The X-ray CT scanner 1 performs the circular orbital scan in the above-mentioned embodiments. However, the invention is not limited to the embodiments. For example, the X-ray CT scanner 1 according to Modified Example 6 performs both the circular orbital scan and the helical scan on the sample P, as shown in FIG. 34. The scan flow in which the circular orbital scan and the helical scan performed under the control of the console controller 13 are combined will be described below.

Figure 35:
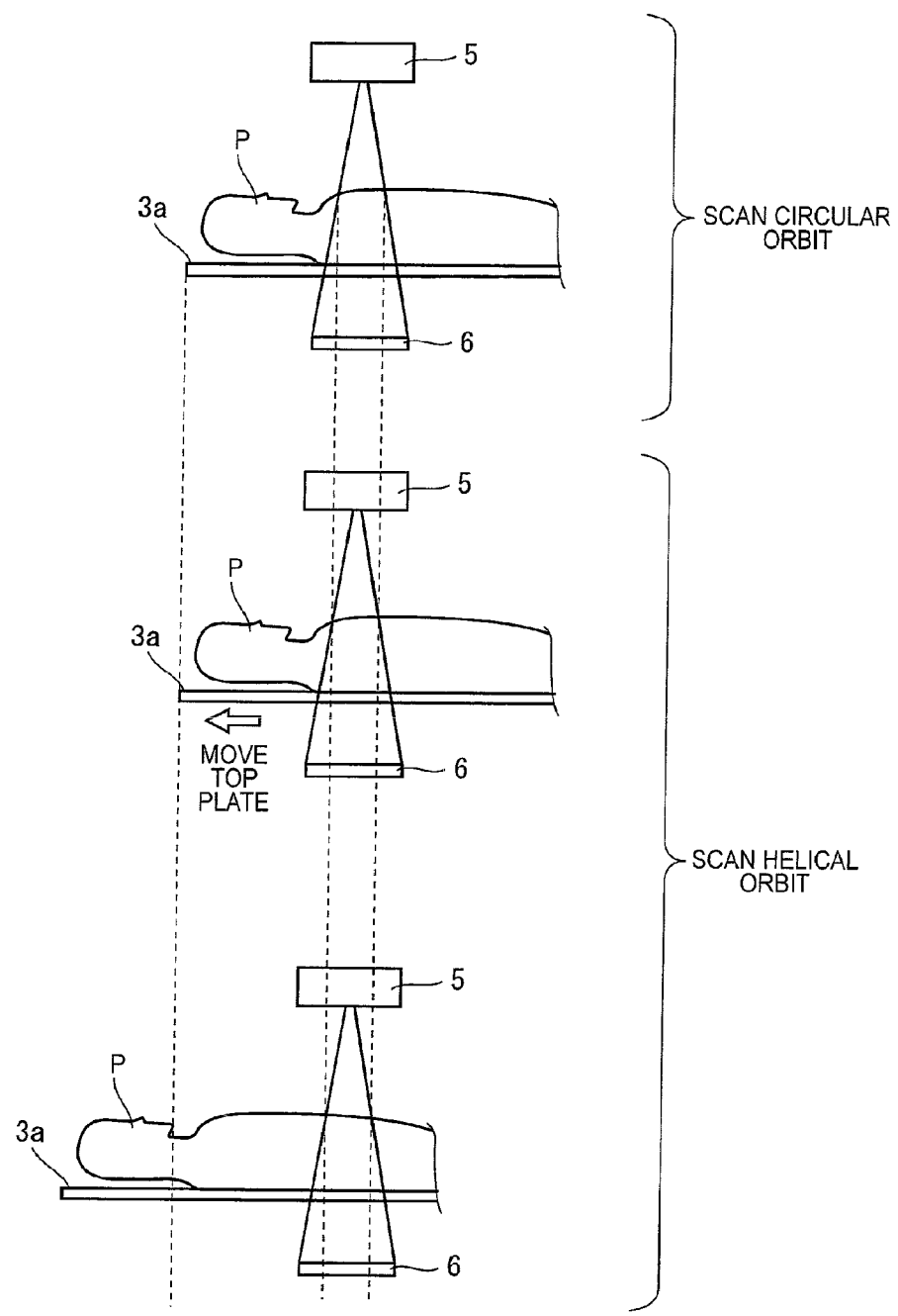
FIG. 35 is a diagram illustrating a flow of a combined scan of the circular orbital scan and the helical scan performed by a console controller according to Modified Example 6 of the invention.
Figure 36:
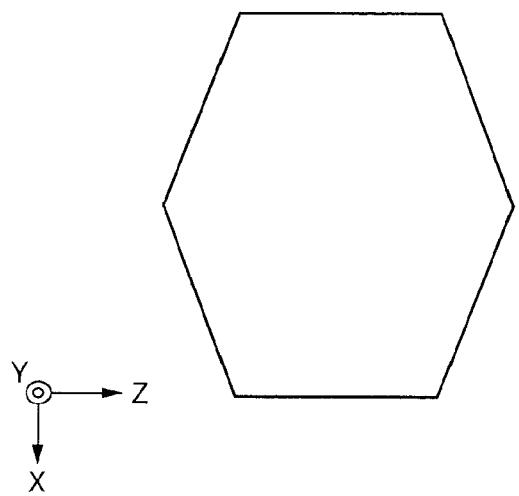
FIG. 36 is a diagram illustrating an example of volume data set on the circular orbital scan shown in FIG. 35.

As shown in FIG. 35, first, the console controller 13 performs a circular orbital scan on the breast of a sample P. The reconstruction processor 17 generates a volume data set on the basis of a projection data set collected by the circular orbital scan. FIG. 36 is a diagram illustrating an example of the volume data set generated from the circular orbital scan.

Figure 37:
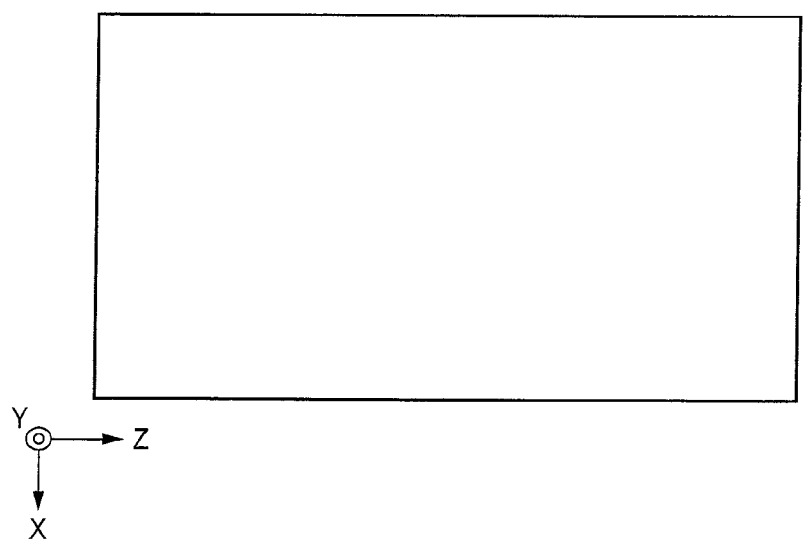
FIG. 37 is a diagram illustrating an example of volume data set on the helical scan shown in FIG. 35.

As shown in FIG. 36, the volume data set acquired by the circular orbital scan has a shape in which a conic shape and a cylindrical shape are combined. When the circular orbital scan is finished, the console controller 13 performs a helical scan from the breast of the sample P to the abdominal region. The reconstruction processor 17 generates a volume data set on the basis of a projection data set collected by the helical scan. FIG. 37 is a diagram illustrating an example of the volume data set generated by the helical scan. As shown in FIG. 37, the volume data set acquired by the helical scan has a cylindrical shape. The scan position of the circular orbital scan and the scan position at the time of starting the helical scan are typically equal to each other.

Figure 38:
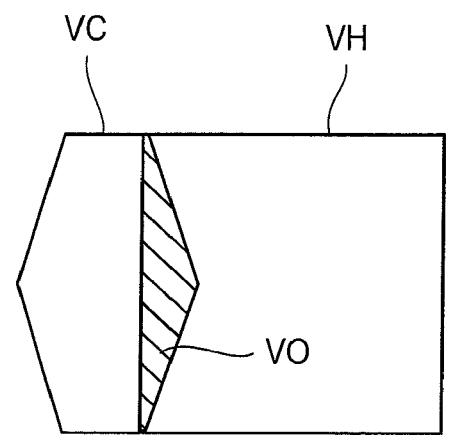
FIG. 38 is a diagram illustrating an example of overlap of the volume data set shown in FIG. 36 and the volume data set shown in FIG. 37.
Figure 39:
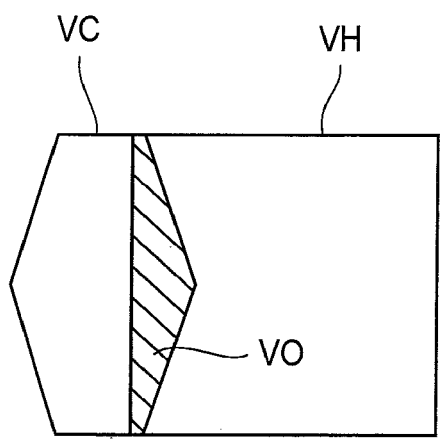
FIG. 39 is a diagram illustrating another example of overlap of the volume data set shown in FIG. 36 and the volume data set shown in FIG. 37.

When the helical scan is finished, the boundary corrector 19 performs a boundary correcting process on the volume data set from the circular orbital scan and the volume data set from the helical scan. The overlapping portion VO of the volume data set VC from the circular orbital scan and the volume data set VH from the helical scan may have a conic shape as shown in FIG. 38, or may have a shape in which a cylindrical shape and a conic shape are combined as shown in FIG. 39. In other words, the boundary corrector 19 can perform the boundary correcting process on the volume data set VC and the volume data set VH, regardless of the method of causing the scan area of the circular orbital scan and the scan area of the helical scan to overlap with each other.

Modified Example 7

Figure 40:
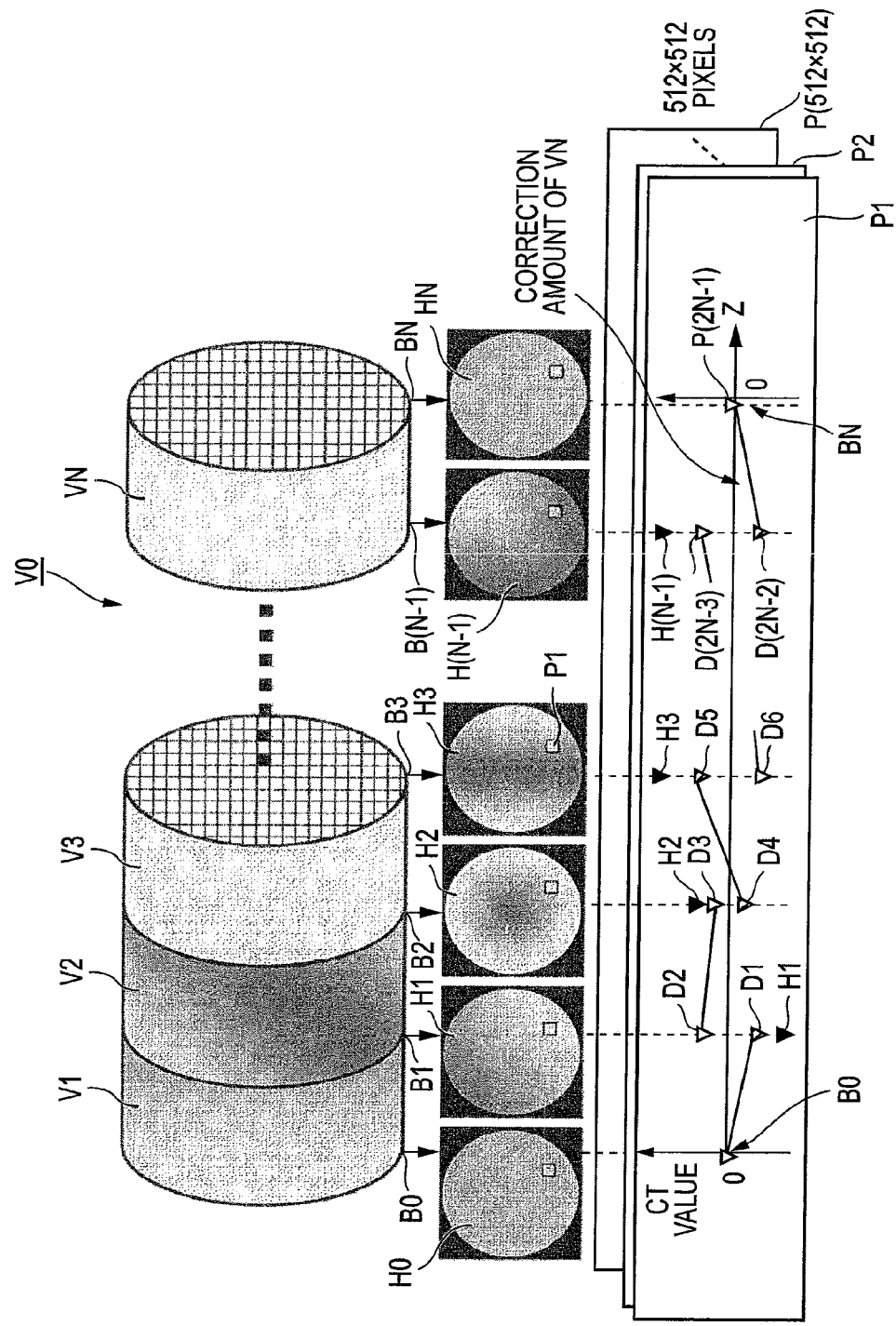
FIG. 40 is a diagram illustrating a boundary correcting process performed by a boundary corrector according to Modified Example 7 of the invention.

The X-ray CT scanner 1 performs three times of circular orbital scans in the above-mentioned embodiments. However, the invention is not limited to the embodiments. For example, the X-ray CT scanner 1 may perform N (N≥2) times of circular orbital scans as shown in FIG. 40. Accordingly, N (N≥2) scan areas are scanned. The boundary corrector 19 according to Modified Example 7 can perform the boundary correcting process on N (N≥2) volume data sets from the N circular orbital scans.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography scanner comprising:
an X-ray tube generating X-rays;
an X-ray detector detecting the X-rays generated from the X-ray tube and transmitted by a sample;
a first support mechanism supporting the X-ray tube and the X-ray detector to be rotatable about a rotation axis;
a second support mechanism supporting the sample to be movable along the rotation axis;
a controller controlling the first support mechanism and the second support mechanism so as to scan a plurality of scan areas partially overlapping or being adjacent along the rotation axis by a plurality of times;
a generator generating a plurality of volume data sets corresponding to the plurality of scan areas on the basis of the output from the X-ray detector; and
a boundary corrector correcting CT values of the plurality of volume data sets on the basis of the CT values in the boundaries between the plurality of volume data sets, wherein the boundaries are overlapping portions or adjacent portions of the plurality of volume data sets, the boundary corrector calculates a correction amount on the basis of the CT value difference between the overlapping portions or the adjacent portions of the plurality of volume data sets and corrects the CT values of the overlapping portions or the adjacent portions on the basis of the calculated correction amount, and the boundary corrector calculates the correction amount of non-overlapping portions or the adjacent portions in the volume data sets on the basis of a middle value of the CT value differences and distances from the overlapping portions or the adjacent portions to the other portions.

2. The X-ray computed tomography scanner according to claim 1, further comprising a synthesizer generating a single synthesized volume data set on the plurality of scan areas on the basis of the plurality of volume data sets corrected by the boundary corrector.

3. The X-ray computed tomography scanner according to claim 1, further comprising a synthesizer generating a single synthesized volume data set on the plurality of scan areas on the basis of the plurality of volume data sets,
wherein the boundary corrector improves the continuity of the spatial variation in CT values in the synthesized volume data set on the basis of the CT value differences between the boundaries included in the synthesized volume data set.

4. The X-ray computed tomography scanner according to claim 1, wherein the boundary corrector multiplies the CT values of the overlapping portions by a weight.

5. The X-ray computed tomography scanner according to claim 4, wherein the weight linearly or nonlinearly varies depending on positions along the rotation axis.

6. The X-ray computed tomography scanner according to claim 4, wherein the boundary corrector multiplies the CT values of the overlapping portions by the weight in the course of causing the generator to generate the plurality of volume data sets.

7. The X-ray computed tomography scanner according to claim 4, wherein the total sum of the weights of the overlapping portions at the same position along the rotation axis is 1.

8. The X-ray computed tomography scanner according to claim 4, wherein the boundary corrector multiplies the CT values of all the overlapping portions or the CT values of a cylindrical portion among the overlapping portions by the weight.

9. The X-ray computed tomography scanner according to claim 1, wherein the boundary corrector determines the middle value of the CT value differences as the correction amount.

10. The X-ray computed tomography scanner according to claim 1, wherein each of the plurality of volume data sets includes data of a plurality of section images, and
wherein the overlapping portions include at least one section image of each of the plurality of volume data sets.

11. The X-ray computed tomography scanner according to claim 1, wherein the boundary corrector calculates the correction amount of the non-overlapping portions on the basis of the middle value and the distances by linear interpolation or nonlinear interpolation.

12. The X-ray computed tomography scanner according to claim 1, wherein the boundary corrector reduces or removes a high-frequency component from the boundaries and corrects the CT values of the plurality of volume data sets on the basis of the CT values of the boundaries from which the high-frequency component has been reduced or removed.

13. The X-ray computed tomography scanner according to claim 1, wherein each of the plurality of scan areas has a cylindrical shape having a center axis substantially corresponding to the rotation axis.

14. The X-ray computed tomography scanner according to claim 1, wherein each of the plurality of scan areas has a combined shape of a cylindrical shape and a conic shape.

15. The X-ray computed tomography scanner according to claim 1, wherein the controller controls the first support mechanism and the second support mechanism to perform at least one circular orbital scan.

16. The X-ray computed tomography scanner according to claim 1, wherein the controller controls the first support mechanism and the second support mechanism to alternately repeat the circular orbital scan and the movement of the sample.

17. The X-ray computed tomography scanner according to claim 1, wherein the controller controls the first support mechanism and the second support mechanism to perform at least one helical scan.

18. The X-ray computed tomography scanner according to claim 1, wherein the controller controls the first support mechanism and the second support mechanism to perform a scan of alternately repeating the circular orbital scan and the movement of the sample and a helical scan.

19. The X-ray computed tomography scanner according to claim 1, further comprising a scattered radiation corrector reducing a scattered radiation component included in a plurality of projection data sets resulting from the plurality of scans from the X-ray detector.

20. The X-ray computed tomography scanner according to claim 1, further comprising a radiation quality corrector calculating a correction amount for reducing disturbance of the CT values due to radiation curing by the X-rays for each of the plurality of volume data sets and correcting the CT values of the volume data sets on the basis of the calculated correction amount.

21. The X-ray computed tomography scanner according to claim 1, further comprising an energy corrector calculating a correction amount for reducing non-uniformity in energy of the X-rays depending on positions along the rotation axis for each of the plurality of volume data sets and correcting the CT values of the volume data sets on the basis of the calculated correction amount.

22. The X-ray computed tomography scanner according to claim 1, wherein the boundary corrector corrects the CT values located in the boundaries of the plurality of volume data sets, wherein the boundaries correspond to the plurality of scan areas located at different positions along the rotation axis which partially overlap or are adjacent along the rotation axis.

23. The X-ray computed tomography scanner according to claim 1, wherein the boundary corrector generates CT value difference distribution of the boundaries of the plurality of volume data sets and corrects CT values of the plurality of volume data sets on the basis of the generated CT value difference distribution.

24. An X-ray computed tomography scanner comprising:
an X-ray tube generating X-rays;
an X-ray detector detecting the X-rays generated from the X-ray tube and transmitted by a sample;
a first support mechanism supporting the X-ray tube and the X-ray detector to be rotatable about a rotation axis;
a second support mechanism supporting the sample to be movable along the rotation axis;
a controller controlling the first support mechanism and the second support mechanism so as to scan a plurality of scan areas partially overlapping or being adjacent along the rotation axis by a plurality of times;
a generator generating a plurality of volume data sets corresponding to the plurality of scan areas on the basis of the output from the X-ray detector; and
a boundary corrector correcting CT values of the plurality of volume data sets on the basis of the CT values in the boundaries between the plurality of volume data sets,
wherein the boundaries are overlapping portions or adjacent portions of the plurality of volume data sets,
the boundary corrector calculates a correction amount on the basis of the CT value difference between the overlapping portions or the adjacent portions of the plurality of volume data sets and corrects the CT values of the overlapping portions or the adjacent portions on the basis of the calculated correction amount, and
the boundary corrector sets the correction amount at a center position of non-overlapping portions to zero and calculates the correction amount at positions other than the center position of the non-overlapping portions on the basis of the correction amount of the overlapping portions or the adjacent portions and the correction amount at the center position.

25. An X-ray computed tomography scanner comprising:
an X-ray tube generating X-rays;
an X-ray detector detecting the X-rays generated from the X-ray tube and transmitted by a sample;
a first support mechanism supporting the X-ray tube and the X-ray detector to be rotatable about a rotation axis;
a second support mechanism supporting the sample to be movable along the rotation axis;
a controller controlling the first support mechanism and the second support mechanism so as to scan a plurality of scan areas partially overlapping or being adjacent along the rotation axis by a plurality of times;
a generator generating a plurality of volume data sets corresponding to the plurality of scan areas on the basis of the output from the X-ray detector; and
a boundary corrector correcting CT values of the plurality of volume data sets on the basis of the CT values in the boundaries between the plurality of volume data sets,
wherein the boundaries are overlapping portions or adjacent portions of the plurality of volume data sets,
the boundary corrector calculates a correction amount on the basis of the CT value difference between the overlapping portions or the adjacent portions of the plurality of volume data sets and corrects the CT values of the overlapping portions or the adjacent portions on the basis of the calculated correction amount, and
the boundary corrector calculates the correction amount of non-overlapping portions on the basis of the correction amount of the overlapping portions or the adjacent portions and the correction amount at the center position.

26. An X-ray computed tomography scanner comprising:
an X-ray tube generating X-rays;
an X-ray detector detecting the X-rays generated from the X-ray tube and transmitted by a sample;
a first support mechanism supporting the X-ray tube and the X-ray detector to be rotatable about a rotation axis;
a second support mechanism supporting the sample to be movable along the rotation axis;

a controller controlling the first support mechanism and the second support mechanism so as to scan a plurality of scan areas overlapping or being adjacent along the rotation axis with the X-rays;

a collector collecting projection data on the plurality of scan areas from the X-ray detector; and a boundary corrector correcting the projection data on overlapping or adjacent portions of the plurality of scan areas among the projection data on the basis of positions of the overlapping or adjacent portions along the rotation axis, wherein multiple images corresponding to at least the partially overlapping boundaries, wherein the boundaries are overlapping portions or adjacent portions of the projection data, the boundary corrector calculates a correction amount on the basis of the CT value difference between the overlapping portions or the adjacent portions of the projection data and corrects the CT values of the overlapping portions or the adjacent portions on the basis of the calculated correction amount, and the boundary corrector calculates the correction amount of non-overlapping portions or the adjacent portions in the projection data on the basis of a middle value of the CT value differences and distances from the overlapping portions or the adjacent portions to the other portions.

27. An X-ray computed tomography scanner comprising:

a storage unit storing a plurality of volume data sets from a plurality of scan areas; and a boundary corrector correcting CT values of the plurality of volume data sets on the basis of the CT values of boundaries among the plurality of volume data sets, wherein multiple images corresponding to at least the partially overlapping boundaries, wherein the boundaries are overlapping portions or adjacent portions of the plurality of volume data sets, the boundary corrector calculates a correction amount on the basis of the CT value difference between the overlapping portions or the adjacent portions of the plurality of volume data sets and corrects the CT values of the overlapping portions or the adjacent portions on the basis of the calculated correction amount, and the boundary corrector calculates the correction amount of non-overlapping portions or the adjacent portions in the volume data sets on the basis of a middle value of the CT value differences and distances from the overlapping portions or the adjacent portions to the other portions.

28. A controlling method of an X-ray computed tomography scanner including:

an X-ray tube generating X-rays;

an X-ray detector detecting the X-rays generated from the X-ray tube and transmitted by a sample;

a first support mechanism supporting the X-ray tube and the X-ray detector to be rotatable about a rotation axis;

a second support mechanism supporting the sample to be movable along the rotation axis; and a controller controlling the first support mechanism and the second support mechanism so as to scan a plurality of scan areas located at different positions along the rotation axis with the X-rays, the controlling method comprising:

generating a plurality of volume data sets from the plurality of scan areas on the basis of the output from the X-ray detector; and correcting CT values of the plurality of volume data sets on the basis of CT value differences between two overlapping or adjacent boundary surfaces among the plurality of volume data sets, wherein multiple images corresponding to at least the partially overlapping boundaries, wherein the correcting of the CT values includes:

calculating CT value differences between two boundary surfaces;

setting two correction amounts of the two boundary surfaces on the basis of a middle value of the CT value differences; and calculating a correction amount of a portion other than the boundary surfaces of the volume data sets by linear interpolation or nonlinear interpolation using the correction amounts of the CT values of the boundary surfaces.

* * * * *